United States Patent
Yamaguchi et al.

(10) Patent No.: US 10,310,245 B2
(45) Date of Patent: Jun. 4, 2019

(54) OPTICAL MICROSCOPE DEVICE, MICROSCOPIC OBSERVATION METHOD AND COMPUTER PROGRAM FOR MICROSCOPIC OBSERVATION USING SINGLE LIGHT-EMITTING PARTICLE DETECTION TECHNIQUE

(71) Applicant: OLYMPUS CORPORATION, Tokyo (JP)

(72) Inventors: Mitsushiro Yamaguchi, Hachioji (JP); Tetsuya Tanabe, Tokyo (JP)

(73) Assignee: OLYMPUS CORPORATION, Hachioji-shi (JP)

(*) Notice: Subject to any disclaimer, the term of this patent is extended or adjusted under 35 U.S.C. 154(b) by 494 days.

(21) Appl. No.: 15/002,992

(22) Filed: Jan. 21, 2016

(65) Prior Publication Data

US 2016/0139392 A1    May 19, 2016
US 2018/0356620 A9    Dec. 13, 2018

Related U.S. Application Data

(63) Continuation of application No. PCT/JP2014/066541, filed on Jun. 23, 2014.

(30) Foreign Application Priority Data

Jul. 31, 2013 (JP) .................. 2013-158897

(51) Int. Cl.
    *G02B 21/00*      (2006.01)
    *G01N 21/64*      (2006.01)

(52) U.S. Cl.
    CPC ..... *G02B 21/0084* (2013.01); *G01N 21/6408* (2013.01); *G01N 21/6458* (2013.01);
(Continued)

(58) Field of Classification Search
    CPC ............ G02B 21/00; G02B 21/0084; G02B 21/0076; G02B 21/22; G02B 21/26;
(Continued)

(56) References Cited

U.S. PATENT DOCUMENTS 4,251,733 A    2/1981   Hirleman, Jr.
4,979,824 A    12/1990   Mathies et al.
(Continued)

FOREIGN PATENT DOCUMENTS

CN     102782480 A    11/2012
EP     1 906 172 A1    4/2008
(Continued)

OTHER PUBLICATIONS

Park, Mira et al., "Counting the Number of Fluorophores Labeled in Biomolecules by Observing the Fluorescence-Intensity Transient of a Single Molecule", Bulletin of the Chemical Society of Japan, Aug. 30, 2005, vol. 78, No. 9, pp. 1612-1618.
(Continued)

*Primary Examiner* — Jie Lei
(74) *Attorney, Agent, or Firm* — Westerman, Hattori, Daniels & Adrian, LLP

(57) ABSTRACT

There is provided a microscopic observation technique capable of detecting a light-emitting object or a light-emitting particle moving in a thick sample by the scanning molecule counting method. In the inventive technique, the light from a light detection region of is detected the optical system of a confocal or multiphoton microscope is detected with while moving the light detection region in each observed subregion obtained by dividing a region to be observed into plural regions; the signal of the light from a light-emitting particle is individually detected; and the position of the light-emitting particle corresponding to the detected signal is determined in the region to be observed.

(Continued)

The moving of the position of the light detection region in each observed subregion is performed continuously in at least two directions or and/or continuously multiple times in each observed subregion.

12 Claims, 8 Drawing Sheets

(52) U.S. Cl.
CPC ....... *G02B 21/008* (2013.01); *G02B 21/0032* (2013.01); *G02B 21/0076* (2013.01); *G02B 21/0088* (2013.01); *G02B 21/0048* (2013.01)

(58) Field of Classification Search
CPC .... G02B 21/248; G02B 21/361; G02B 21/24; G02B 21/0048; G02B 21/0088; G02B 21/0032; G02B 21/008; G01J 1/42; G01J 1/58; G01S 3/786; G01N 21/428; G01N 15/02; G01N 23/00; G01N 21/6408; G01N 21/6458
USPC ........ 359/393, 381, 363, 368, 369; 250/200, 250/203.3, 459.1, 458.1
See application file for complete search history.

(56) References Cited

U.S. PATENT DOCUMENTS

| | | | |
|---|---|---|---|
| 5,866,336 | A | 2/1999 | Nazarenko et al. |
| 5,936,764 | A | 8/1999 | Kobayashi |
| 6,280,960 | B1 | 8/2001 | Carr |
| 6,376,843 | B1 | 4/2002 | Palo |
| 6,388,746 | B1 | 5/2002 | Eriksson et al. |
| 6,388,788 | B1 | 5/2002 | Harris et al. |
| 6,400,487 | B1 | 6/2002 | Harris et al. |
| 6,403,338 | B1 | 6/2002 | Knapp et al. |
| 6,563,583 | B2 | 5/2003 | Ortyn et al. |
| 6,710,871 | B1 | 3/2004 | Goix |
| 6,782,297 | B2 | 8/2004 | Tabor |
| 6,856,391 | B2 | 2/2005 | Garab et al. |
| 6,927,401 | B1 | 8/2005 | Palo |
| 8,284,484 | B2 | 10/2012 | Hoult et al. |
| 8,471,220 | B2 * | 6/2013 | Yamaguchi ........ G01N 15/1456 250/458.1 |
| 9,188,535 | B2 * | 11/2015 | Hanashi ............. G01N 15/1429 |
| 9,423,349 | B2 * | 8/2016 | Tanabe ............... G01N 21/6452 |
| 2001/0035954 | A1 | 11/2001 | Rahn et al. |
| 2002/0008211 | A1 | 1/2002 | Kask |
| 2002/0036775 | A1 | 3/2002 | Wolleschensky et al. |
| 2002/0180965 | A1 | 12/2002 | Engelhardt et al. |
| 2003/0036855 | A1 | 2/2003 | Harris et al. |
| 2003/0218746 | A1 | 11/2003 | Sampas |
| 2004/0022684 | A1 | 2/2004 | Heinze et al. |
| 2004/0051051 | A1 | 3/2004 | Kato et al. |
| 2004/0150880 | A1 | 8/2004 | Nakata et al. |
| 2005/0260660 | A1 | 11/2005 | van Dongen et al. |
| 2006/0078998 | A1 | 4/2006 | Puskas et al. |
| 2006/0158721 | A1 | 7/2006 | Nakata et al. |
| 2006/0256338 | A1 | 11/2006 | Gratton et al. |
| 2007/0206192 | A1 | 9/2007 | Fomitchov et al. |
| 2007/0250274 | A1 | 10/2007 | Volkov et al. |
| 2008/0052009 | A1 | 2/2008 | Chiu et al. |
| 2009/0159812 | A1 | 6/2009 | Livingston |
| 2010/0033718 | A1 | 2/2010 | Tanaami |
| 2010/0177190 | A1 | 7/2010 | Chiang et al. |
| 2010/0202043 | A1 | 8/2010 | Ujike |
| 2013/0314705 | A1 | 11/2013 | Tanabe et al. |
| 2014/0162268 | A1 | 6/2014 | Tanabe et al. |
| 2014/0162378 | A1 | 6/2014 | Hanashi |
| 2014/0170760 | A1 | 6/2014 | Tanabe et al. |

FOREIGN PATENT DOCUMENTS

| | | |
|---|---|---|
| JP | 04337446 A | 11/1992 |
| JP | 2002-507762 A | 3/2002 |
| JP | 2002-543414 A | 12/2002 |
| JP | 2004-506192 A | 2/2004 |
| JP | 2005-017642 A | 1/2005 |
| JP | 2005-098876 A | 4/2005 |
| JP | 2005-099662 A | 4/2005 |
| JP | 2005/300292 A | 10/2005 |
| JP | 2006-162994 A | 6/2006 |
| JP | 2007-020565 A | 2/2007 |
| JP | 4023523 B2 | 12/2007 |
| JP | 2008-116440 A | 5/2008 |
| JP | 2008-536093 A | 9/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| WO | 1998/016814 A1 | 4/1998 |
| WO | 1999/047963 A | 9/1999 |
| WO | 2000/066985 A1 | 11/2000 |
| WO | 2002/012864 A1 | 2/2002 |
| WO | 2012/053355 A1 | 4/2002 |
| WO | 2006/084283 A2 | 8/2006 |
| WO | 2007/010803 A1 | 1/2007 |
| WO | 2007/118209 A2 | 10/2007 |
| WO | 2007/147159 A2 | 12/2007 |
| WO | 2008/007580 A1 | 1/2008 |
| WO | 2008/080417 A1 | 7/2008 |
| WO | 2009/087392 A1 | 7/2009 |
| WO | 2009/117033 A2 | 9/2009 |
| WO | 2011/108369 A1 | 9/2011 |
| WO | 2011/108370 A1 | 9/2011 |
| WO | 2011/108371 A1 | 9/2011 |
| WO | 2012/050011 A1 | 4/2012 |
| WO | 2013/024650 A1 | 2/2013 |
| WO | 2013/031365 A1 | 3/2013 |
| WO | 2013/031439 A1 | 3/2013 |

OTHER PUBLICATIONS

U.S. Office Action dated Apr. 2, 2013, issued in related U.S. Appl. No. 13/596,280 (7 pages).
Kask, Peet et al., "Two-Dimensional Fluorescence Intensity Distribution Analysis: Theory and Applications", Biophysical Journal, Apr. 2000, vol. 78, pp. 1703-1713.
Chinese Office Action dated Aug. 13, 2013, issued in related Chinese application No. 201180011655.3; w/ English Translation (16 pages).
International Search Report dated Mar. 29, 2011, issued in related PCT/JP2011/053483.
International Preliminary Report on Patentability (PCT/IPEA/409) issued in related PCT/JP2011/053483.
Chinese Office Action dated Aug. 9, 2013, issued in related Chinese application No. 201180011640.7; w/ English Translation (16 pages).
International Search Report dated Mar. 29, 2011, issued in related PCT/JP2011/053482.
International Preliminary Report on Patentability (PCT/IPEA/409) issued in related PCT/JP2011/053482.
U.S. Office Action dated Jan. 3, 2013, issued in related U.S. Appl. No. 13/597,825 (5 pages).
Chinese Office Action dated Feb. 7, 2013, issued in related Chinese application No. 201180011644.5; w/ English Translation (19 pages).
Extended European Search Report dated Mar. 28, 2013, issued in related EP application No. 11750481.1.
International Search Report dated Mar. 29, 2011, issued in related PCT/JP2011/053481.
International Preliminary Report on Patentability (PCT/IPEA/409) issued in related PCT/JP2011/053481.
Goodwin, Peter et al., "Rapid Sizing of Individual Fluorescently Stained DNA Fragments by Flow Cytometry", Nucleic Acids Research, 1993, vol. 21, No. 4, pp. 803-806.
Keller, Richard et al., "Single-Molecule Fluorescence Analysis in Solution", Applied Spectroscopy, 1996, vol. 50, No. 7, pp. 12A-32A.

(56) References Cited

OTHER PUBLICATIONS

Lee, Yuan-Hsiang et al., "Laser-Induced Fluorescence Detection of a Single Molecule in a Capillary", Analytical Chemistry, Dec. 1, 1994, vol. 66, No. 23, pp. 4142-4149.
Li, Haitao et al., "Ultrasensitive Coincidence Fluorescence Detection of Single DNA Molecules", Analytical Chemistry, Apr. 1, 2003, vol. 75, No. 7, pp. 1664-1670.
Nie, Shuming et al., "Probing Individual Molecules with Confocal Fluorescence Microscopy", Science, Nov. 11, 1994, vol. 266, pp. 1018-1021.
Tahari, Abdel. "Fluorescence Correlation Spectroscopy: Ultrasensitive Detection in Clear and Turbid Media", University of Illinois, 2006, pp. 1-88.
WU, Alan et al., "Development and Preliminary Clinical Validation of a High Sensitivity Assay for Cardiac Troponin Using a Capillary Flow (Single Molecule) Fluorescence Detector", Clinical Chemistry, 2006, vol. 52, No. 11, pp. 2157-2159.
Itoh et al., "A New Method for Detection of Influenza Viruses by Single Particle-Recognition Based on the Principle of Fluorescence Correlation Spectroscopy", Chemistry and Biology, 2009, vol. 47, No. 12, pp. 823-830.
Carlsson, K. et al., "Three-dimensional Microscopy Using a Confocal Laser Scanning Microscope", Optics Letters, Optical Society of America, Feb. 1985, vol. 10, No. 2, pp. 53-55, XP007922413.
U.S. Office Action dated Oct. 4, 2013, issued in related U.S. Appl. No. 13/596,243 (7 pages).
Japanese Office Action dated Dec. 18, 2012, issued in related JP application No. 2012-503060; w/ English Translation (6 pages).
Written Opinion of International Searching Authority dated Aug. 13, 2013, issued in related PCT/JP2013/063688.
U.S. Notice of Allowance dated Mar. 27, 2013, issued in related U.S. Appl. No. 13/597,825 (8 pages).
International Search Report dated Sep. 2, 2014, issued in related PCT/JP2014/066541.
Kask, Peet et al. "Fluorescence-Intensity Distribution Analysis and its Application in Biomolecular Detection Technology", PNAS, Nov. 23, 1999, vol. 96, No. 24, pp. 13756-13761.
Kinjo, M. "Single Molecule Detection by Fluorescence Correlation Spectroscopy", Proteins, Nucleic Acids and Enzymes, 1999, vol. 44, No. 9, pp. 1431-1438.
Meyer-Almes, F. J. "A New Method for Use in Molecular Diagnostics and High Throughput Pharmaceutical Screening based on Fluorescence Correlation Spectroscopy", Nanoparticle Immunoassays, R. Ridger, edit., Springer, Berlin, 2000, pp. 204-224.
Kato, N. et al., "A Single Molecule Analyzer that Enables New Analysis of DNA and Protein Interactions", Gene & Medicine, 2002, vol. 6, No. 2, pp. 271-277.
Extended European Search Report dated Oct. 20, 2014, issued in related EP application No. 12770835.2.
Final Office Action dated Sep. 28, 2015 issued in co-pending U.S. Appl. No. 13/746,968.
Final Office Action dated Sep. 29, 2015 issued in co-pending U.S. Appl. No. 13/946,091.
Office Action dated Jun. 1, 2017, issued in counterpart Chinese Application No. 201480043252.0, with English translation (25 pages).
Levi, Valeria et al., "3-DParticle Tracking in a Two-Photon Microscope: Application to the Study of Molecular Dynamics in Cells", Biophysical Journal, vol. 88, No. 4, Apr. 1, 2005, pp. 2919-2928.
Oishi, M. et al., "Simultaneous measurement of internal and surrounding flows of a moving droplet using multicolour confocal micro-particle image velocimetry (micro-PIV)", Measurement Science and Technology, IOP Publishing, vol. 22, No. 10, Aug. 19, 2011, pp. 1-13.
Erdel, Fabian et al., "Dissecting chromatin interactions in living cells from protein mobility maps", Chromosome Reasearch, Kluwer Academic Publishers, vol. 19, No. 1, Sep. 17, 2010, pp. 99-115.
(Supplementary) Search Report dated Feb. 13, 2017, issued in counterpart European Application No. 14832322.3 (8 pages).
Extended European Search Report dated Oct. 2, 2017, issued in related European patent application No. 11750482.9.
Extended European Search Report dated Sep. 29, 2017, issued in related European patent application No. 11750483.7.
Office Action dated Mar. 13, 2018, issued in counterpart Japanese Application No. 2015-529456, with English translation. (8 pages).
Office Action dated Mar. 20, 2019, issued in related EP Application No. 11 750 482.9 (6 pages).

* cited by examiner

FIG.1A
FIG.1B
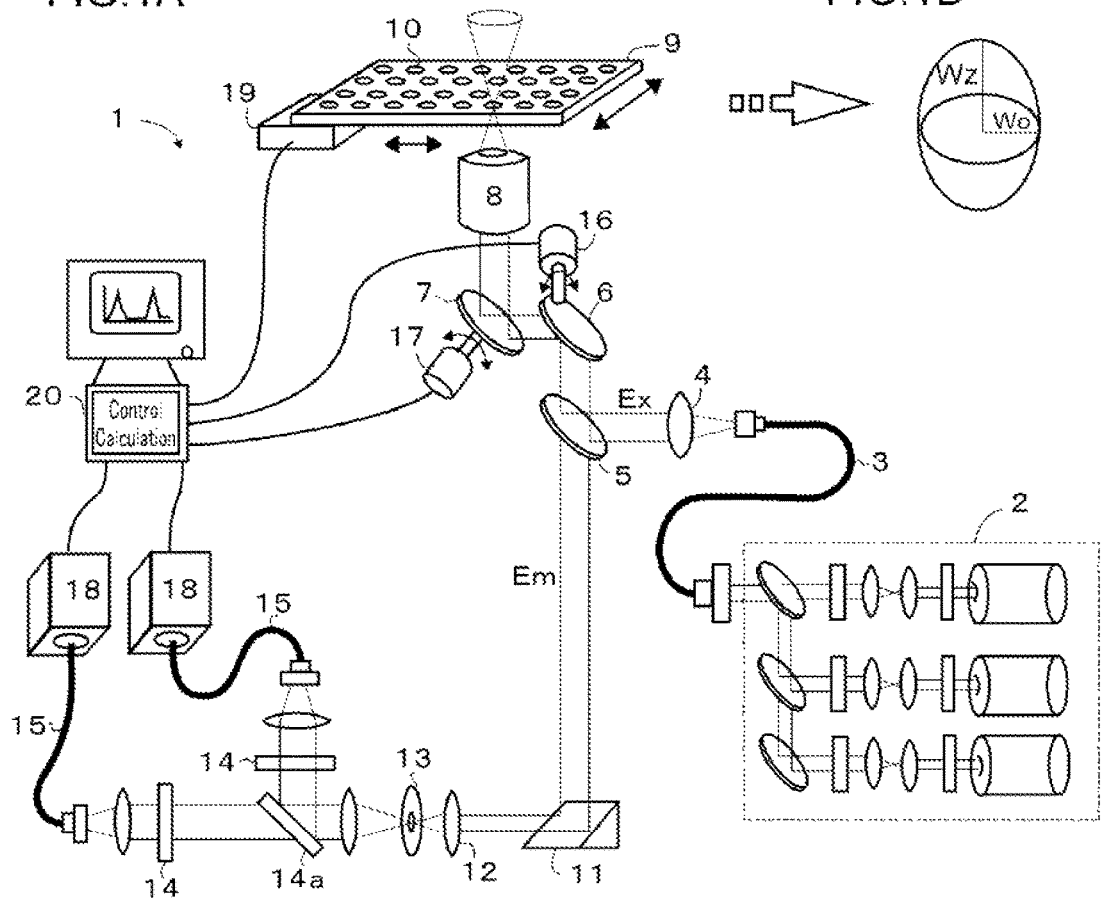
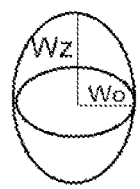
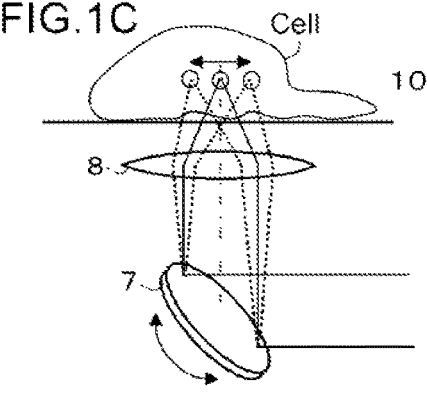
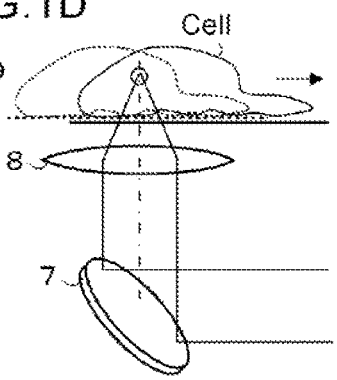

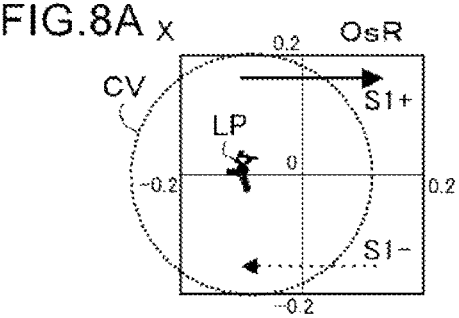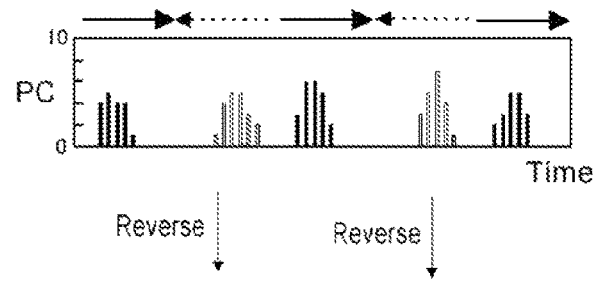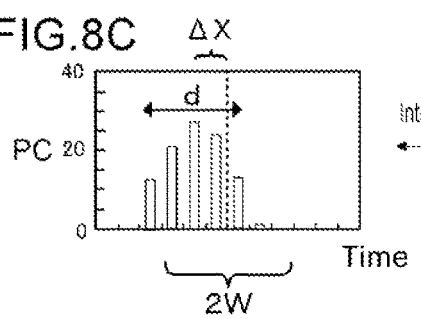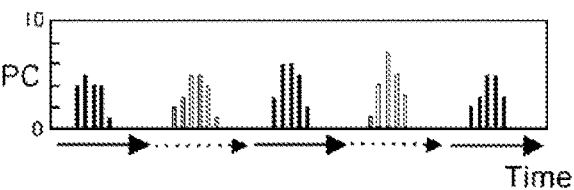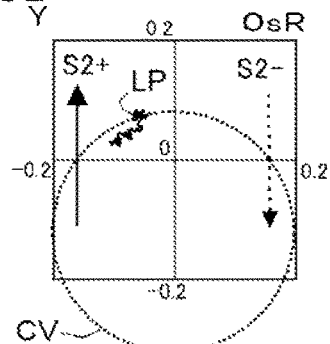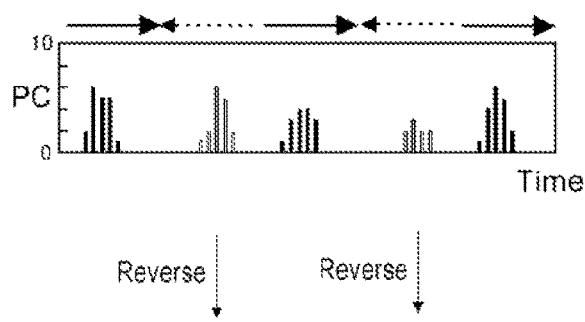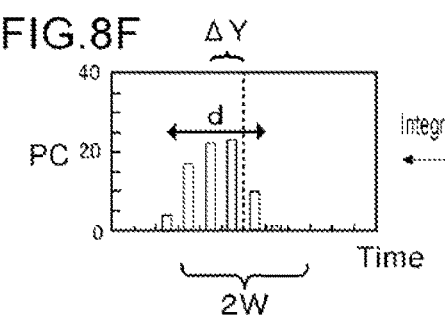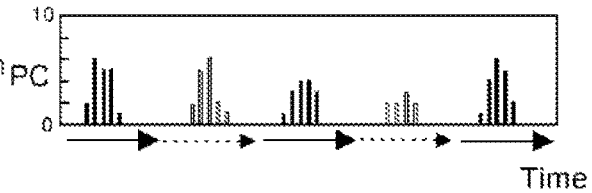

OPTICAL MICROSCOPE DEVICE, MICROSCOPIC OBSERVATION METHOD AND COMPUTER PROGRAM FOR MICROSCOPIC OBSERVATION USING SINGLE LIGHT-EMITTING PARTICLE DETECTION TECHNIQUE

TECHNICAL FIELD

This invention relates to optical microscopic observation techniques for detecting and imaging an atom, a molecule or these aggregate in a liquid (Hereafter, these are called a "particle"), for example, a biomolecule, such as protein, peptide, nucleic acid, lipid, sugar chain, amino acid or these aggregate, a particulate object, such as a virus and a cell; or a non-biological particle, and more specifically, to optical microscope devices, microscopic observation methods and computer programs for microscopic observation, using a single light-emitting particle detection technique which detects individually the light from a single particle by means of an optical system which can detect light from a micro area in a solution, such as the optical system of a confocal microscope or a multiphoton microscope. In this regard, in this specification, a particle which emits light (Hereinafter, referred to as a "light-emitting particle") may be a particle which emits light by itself or a particle to which an arbitrary light-emitting label or light-emitting probe is attached, and the light emitted from a light-emitting particle may be fluorescence, phosphorescence, chemoluminescence, bioluminescence, scattering light, etc.

BACKGROUND ART

According to the developments of optical measurement techniques in recent years, there have become possible the observation with an optical microscope and the capturing of a microscopic image (the determination of the position of a two-dimensional or three-dimensional image) through the detection and measurement of faint light at a single fluorescent molecule level. For instance, as described in patent document 1, etc., in accordance with a microscope device consisting of a laser scan type confocal microscope and a super sensitive photodetector, a condition in a sample is imaged by detecting light from a micro region which is a region where the light is detected in the microscope (Hereinafter, referred to as a "light detection region") while moving the light detection region in the sample so as to scan the inside of the sample. In the case of the optical system of such a confocal microscope, since the light emitted from the outside of the light detection region is blocked and not allowed to reach the photodetector, the detection and measurement of the faint light at a single fluorescent molecule level or a single photon level are possible, and therefore, the imaging with such faint light becomes possible. Further, as an alternative way of the optical microscopic observation and the capturing of a microscopic image with faint light at a single fluorescent molecule level, as described in patent document 2, etc., there have been proposed microscope devices using evanescent light, also. In the cases of such microscope devices using evanescent light, excitation light is given only to a thin region of about 100 nm near the surface of a cover glass and there occurs no light emission from regions other than the thin region, and thus, background light in a microscopic image is greatly reduced, and thereby, an image with faint light at a single fluorescent molecule level or a single photon level will be obtained.

By the way, in patent documents 3-8, etc., Applicant of the present application proposed a new optical analysis technique which enables detecting a light-emitting particle distributed or dissolved in liquid (hereinafter, referred to as "scanning molecule counting method"). In this scanning molecule counting method, the optical system, such as those of a confocal microscope and a multiphoton microscope, which can detect light from a micro area in solution, is used, in which the position of the light detection region is moved, namely, the inside of the sample solution is scanned with the light detection region, and when the light detection region encompasses a light-emitting particle distributed and moving at random in the sample solution, the light emitted from the light-emitting particle is detected individually, and thereby, one by one, light-emitting particles in the sample solution are detected so that the counting of the light-emitting particles and the acquisition of the information on the concentration or the number density of the light-emitting particles in the sample solution becomes possible.

PRIOR TECHNICAL DOCUMENTS

Patent Documents

[Patent document 1] JP2005-017642
[Patent document 2] JP 2006-162994
[Patent document 3] WO2011/108369
[Patent document 4] WO2011/108370
[Patent document 5] WO2011/108371
[Patent document 6] WO2012/050011
[Patent document 7] WO2012/053355
[Patent document 8] WO2013/031439

SUMMARY OF INVENTION

Technical Problem

In the cases of the above-mentioned laser scan type confocal microscope devices, typically, a region to be observed is scanned in two dimensions or three dimensions in the raster scan mode, and the detected light intensity values are associated with the position information in the region to be observed so that a microscopic image will be formed. In the case of this raster scan mode, usually, an image in a region to be observed is formed by reciprocating a light detection region in a certain one direction within the region to be observed while displacing the route of the reciprocation of the light detection region in the other direction. In that case, when the detected light intensity is weak, the scanning of the same region is repeated so that the light intensities will be integrated. In the case of this structure, however, an image of a light-emitting object or a light-emitting particle which substantially remains at rest within a region to be observed during the time taken by the scanning of the region to be observed can be clearly formed, but, with respect to a light-emitting object or a light-emitting particle in a dynamic condition owing to diffusion, transport phenomenon, etc., the position of the light-emitting object or light-emitting particle is moved during multiple times of the scanning of the region to be observed, and thus, no effective integration effect will be obtained. On the other hand, in the case of the microscope device using evanescent light, since a region to be observed will be limited only to the surface of a cover glass, it is difficult to carry out the imaging of light-emitting objects or light-emitting particles in a thick sample.

By the way, as already noted, according to the way of the scanning molecule counting method in which, using the optical system of a confocal microscope or a multiphoton microscope, the existence of a light-emitting particle is detected during moving a light detection region in liquid, it is possible to detect faint light from a light-emitting object or a light-emitting particle whose position dynamically changes in a thick sample. Accordingly, by utilizing the way of the scanning molecule counting method in the imaging in a microscopic observation, the formation of an image of a light-emitting object or a light-emitting particle whose position changes dynamically in a thick sample will be achieved.

Thus, the main object of the present invention is to provide a microscope device, a microscopic observation method and a computer program for those, which are capable of the formation of an image of a light-emitting object or a light-emitting particle whose position dynamically changes in a thick sample by utilizing the way of the scanning molecule counting method.

Solution to Problem

According to one manner of the present invention, the above-mentioned object is achieved by an optical microscope device which detects light from a light-emitting particle in a sample liquid to detect the light-emitting particle, using an optical system of a confocal microscope or a multiphoton microscope, the device comprising: a light detection region mover which moves a position of a light detection region multiple times continuously within each observed subregion, the respective observed subregions being obtained by dividing a region to be observed in a field of view of the microscope into plural regions; a light detector which detects light from the light detection region; and a signal processor which generates time series light intensity data of the light from the light detection region detected by the light detector while moving the position of the light detection region in each observed subregion, detects a signal having a characteristic of a signal indicating light from each light-emitting particle individually in the time series light intensity data, and determines a position of each light-emitting particle corresponding to the detected signal in the region to be observed.

In the above-mentioned structure, "a light-emitting particle which moves in a sample liquid" may be a particle which emits light, for example, an atom, a molecules or an aggregate of those in a condition that it can move within an arbitrary liquid, such as in a cell, in a cell organelle. The light-emitting particle is typically a fluorescent particle, but may be a particle which emits light by phosphorescence, chemoluminescence, bioluminescence, scattering light, etc. The "light detection region" of the optical system of a confocal microscope or a multiphoton microscope is a micro area from which light is detected in those microscopes, and corresponds to the region to which illumination light is condensed when it is given from an objective (In a confocal microscope, the "light detection region" is defined by the spatial relationship between an objective and a pinhole). The "region to be observed" is a two- or three-dimensional region in the field of view of a microscope, in which region the imaging is carried out in the present device, and the "observed subregion" is each of a plurality of regions obtained by virtually dividing the "region to be observed" into plural regions in a lattice or grid pattern. Further, the light detector may be a structure using a photodetector of type which detects the light from a light detection region by the photon counting in which the number of photons which arrive in every predetermined measuring unit time (bin time) is counted, and in that case, the time series light intensity data becomes time series photon count data. In this regard, in this specification, a "signal of a light-emitting particle" is meant to be a signal indicating light from a light-emitting particle unless noted otherwise.

As understood from the above, in the basic structure of the present invention, as in a laser scan type confocal microscope or multiphoton microscope, the position of a "light detection region" (confocal volume) is moved within a predetermined two- or three-dimensional space in a sample liquid, namely, a two- or three-dimensional space (a "region to be observed") in a sample liquid is scanned with the light detection region, and thereby, the light emitted from the "region to be observed" is detected. However, in the case of the present invention, especially, the manner of the scanning in the region to be observed with a light detection region and the manner of signal processing of the detected light differ from in usual cases. Namely, in the present invention, the scanning with the light detection region is performed multiple times continuously in the respective observed subregions obtained by virtually dividing the "region to be observed" in a lattice or grid pattern, and when the moving light detection region encompasses a light-emitting particle in the liquid, the light from the light-emitting particle is detected (the light measurement of the scanning molecule counting method). Then, in the process of the so obtained time series light intensity data of the detected light, for each of the observed subregions, the individual detection of a light-emitting particle existing in the region is performed by the manner of detecting the presence or absence of a signal of light from a light-emitting particle (Individual detection of a light-emitting particle of the scanning molecule counting method), and when a light-emitting particle exists, the determination of its position within the region to be observed is conducted. That is, in the structure of the present invention, the principle of the scanning molecule counting method is applied for each observed subregion so as to perform the detection of the existence of a light-emitting particle in a microscopic observation.

According to this structure, since the size of an observed subregion is sufficiently smaller than the size of a region to be observed, the time to be taken by the scanning of each observed subregion at a scanning speed which makes it possible to detect weak light from each light-emitting particle individually and significantly and determine the position of each light-emitting particle will become short. Namely, the scanning time taken for the detection of one light-emitting particle becomes short, and therefore, even in a case that the position of a light-emitting particle changes with time, it can be more surely achieved to detect significantly the light from the light-emitting particle multiple times before its position largely changes. Moreover, in the structure of the present invention, since the position of the light detection region in the sample liquid is not limited to near the surface of a sample container (unlike the microscopic observation method with evanescent light), even for a light-emitting particle moving in a place away from near the surface of the sample container in a thick sample liquid, it is possible to detect its existence and determine its position. What should be understood is that, in the structure of the present invention, since the position of a detected light-emitting particle is determined, the existence position of the light-emitting particle in a region to be observed can be expressed with a two- or three-dimensional image. In this regard, with respect to the position of a light-emitting particle to be determined, first, the position of the observed subregion in the region to be observed is determinable as the position of the light-emitting particle. And alternatively, further, in a certain embodiment of detecting a light-emitting particle, the position of the light-emitting particle in an observed subregion is determinable as explained in the column of Embodiments later.

In the above-mentioned structure, in one manner, the multiple times of successive moving of the position of the light detection region in each observed subregion, i.e., the multiple times of scanning with the light detection region may be carried out continuously in at least two directions in each observed subregion. For example, the scanning in the X direction and the scanning in the Y direction may be performed continuously in one observed subregion, and also, the scanning in the X direction, the scanning in the Y direction and the scanning in the Z direction may be performed continuously in one observed subregion. In that case, as explained in detail in the column of Embodiments later, it becomes possible to determine the position in the X direction and Y direction or the position in the X direction, Y direction and Z direction for a light-emitting particle. Alternatively, the multiple times of scanning with the light detection region in each observed subregion may be continuously conducted in the same one direction. In that case, if a light-emitting particle exists in an observed subregion, the integration of the light will become possible, or, it becomes possible to acquire information on the moving characteristic or translational diffusional characteristic of the light-emitting particle from the variation of the position during multiple times of scanning. What is to be understood here is that, since multiple times of scanning is performed in each observed subregion having a small size, the possibility that one light-emitting particle would deviate from an observed subregion being scanned in the scanning time becomes low, and thus, the possibility that the light of the same light-emitting particle can be detected during scanning multiple times becomes higher (The success rate of detecting the light of the same light-emitting particle during scanning multiple times becomes higher).

The size of the above-mentioned observed subregion decides the time taken for the light detection region to scan the observed subregion, and thus, concretely, it may be determined based on the size of the light detection region. In this respect, as noted above, in order to catch more certainly the light of the same light-emitting particle with the light detection region during scanning multiple times, it is preferable to adjust the size of the observed subregion so that the same light-emitting particle will not deviate during the scanning time. Thus, preferably, the size of an observed subregion is set such that an (expected) moving length of a light-emitting particle to be detected within a time in which the position of the light detection region is moved in the observed subregion becomes smaller than the size of the observed subregion.

Moreover, when the light detection region moves in a certain one way within an observed subregion, the scanning time will become shortened if one time of moving of the light detection region covers the whole observed subregion. Thus, it is preferable that the one side length of an observed subregion is set to be almost the same as the diameter of the light detection region. In this respect, as explained in detail in the column of Embodiments later, in the detection of a light-emitting particle by the scanning molecule counting method, typically, when a light detection region passes through the existence position of a light-emitting particle, a pulse-like time variation of the light intensity having a bell-shaped profile is captured as a signal of light from the light-emitting particle. This bell-shaped profile results from that the variation of the light intensity, emitted from a light-emitting particle in the light detection region and detected, depends upon the position of the light-emitting particle in the light detection region, and the intensity distribution of its light forms a bell-shaped distribution in which a light intensity reduces as the position of a light-emitting particle moves from the almost center in the light detection region toward its periphery. Thus, in order to more certainly catch a signal of light from a light-emitting particle existing in an observed subregion, it is preferable that the bell-shaped profile of the signal of the light from a light-emitting particle appears in time series light intensity data generated from the detected light. On the other hand, a light-emitting particle may exist in the position shifted from the center of an observed subregion. Namely, for all light-emitting particles existing in the whole area of an observed subregion, including also a light-emitting particle existing in the position shifted from the center of the observed subregion, in order to catch the respective bell-shaped profiles of those signals, it is necessary to make the edge portion of the light detection region pass through the whole area of the observed subregion. For this, it will be preferable that the front edge and rear edge of a light detection region in its movement direction pass through the opposite sides (or the opposite faces) of an observed subregion in the movement direction of the light detection region. Thus, in the above-mentioned present invention, it is more preferable that one time of moving of the position of a light detection region in each observed subregion is performed from when the front edge in the movement direction of the light detection region passes through one side edge of the observed subregion and until the rear edge in the movement direction of the light detection region reaches to the other side edge of the observed subregion. In this regard, preferably, the manner of this one time of moving of the position of the light detection region is applied in all the directions (X, Y, Z) in which the scanning is performed. According to this structure, it becomes possible to determine the position in an observed subregion of a light-emitting particle which exists in an observed subregion from the analysis of a bell-shaped profile of a signal of the light-emitting particle (see the column of Embodiments described later).

In the above-mentioned structure, the moving speed of the position of the light detection region in its scanning may be appropriately changeable based on the characteristics of a light-emitting particle to be observed or its number density or concentration in the sample solution. Especially, since the detected light amount will decrease if the moving speed of the light detection region becomes quick, it is preferable that the moving speed of the light detection region can be changed appropriately so that it becomes possible to measure the detected light amount with high precision and/or high sensitivity. In this connection, more preferably, the moving speed of the position of the light detection region is set higher than the diffusion moving velocity of the light-emitting particle (the average moving speed of the particle by the Brownian motion). As already noted, in the inventive observation technique employing the way of the "scanning molecule counting method", the existence of a light-emitting particle is detected by detecting the light from the light-emitting particle when a light detection region encompasses the light-emitting particle, and if the light-emitting particle moves at random by the Brownian motion, and so, the light-emitting particle would enter into and exit out of the light detection region multiple times (during one time of scanning), the signal expressing the existence of the one light-emitting particle would be detected multiple times, and thereby it would become difficult to associate a detected signal with the existence of one light-emitting particle. Thus, as noted above, the moving speed of the light detection region is set higher than the diffusion moving velocity of the light-emitting particle, and thereby, it becomes possible to make one light-emitting particle correspond with one signal (indicating the existence of the light-emitting particle). In this regard, since the diffusion moving velocity changes depending upon a characteristic of a light-emitting particle, it is preferable that the moving speed of the light detection region is changeable appropriately according to the characteristic (especially, the diffusing constant) of the light-emitting particle as noted above.

The moving of the position of the light detection region may be achieved by an arbitrary way. For instance, the position of the light detection region may be changed by changing the optical path in the optical system of the microscope by means of a galvano mirror employed in a laser scan type light microscope, and alternatively, the relative position of the light detection region in the sample solution may be moved by moving the position of the sample solution (e.g. by moving the stage of a microscope). The moving in the direction of the optical axis of an objective is achievable by adjusting the position of the objective in its height direction or the position of the stage in its height direction, or with a mechanism forming the beam light, which enters into and exits out of the back end of an objective, into a convergent beam or a divergent beam (instead of forming a parallel beam).

By the way, in the above-mentioned inventive microscopic observation technique, the way of the individual detection of light-emitting particles in accordance with the scanning molecule counting method is employed, and in the scanning molecule counting method, it is possible to acquire the information on a condition or a characteristic of a light-emitting particle, especially, the size of the light-emitting particle through making it possible to detect the characteristic of its light or the occurrence time of the signal of its light by an arbitrary way (patent documents 6-7). Thus, in the above-mentioned present invention, the signal processor may be constructed to determine the information on the size of a light-emitting particle, by using the characteristics of the signals of the same light-emitting particle obtained during multiple times of moving of the light detection regions in each observed subregion. Such characteristics of the signals of a light-emitting particle, concretely, may be an index value indicating a translational diffusional characteristic of the light-emitting particle and/or an index value indicating a rotational diffusion characteristics of the light-emitting particle. In this regard, in this structure, it should be understood that, in the case of the present invention, the information about the size of each light-emitting particle is acquired under the condition that the position of the light-emitting particle is determined in the region to be observed, or under the condition that the position of the light-emitting particle is expressed as an image.

Moreover, as noted, for a light-emitting particle detected in the present invention, its position in a region to be observed can be determined, and can be represented as an image. So, the position of a light-emitting particle can be superimposed and expressed on a microscopic image (for example, a transmitted light image, an epi-illuminated fluorescence image, etc.) of a region to be observed generated by an arbitrary way. Accordingly, in the inventive device, there may be generated a plot image obtained by plotting the position of a light-emitting particle, whose position in a region to be observed has been determined, on a microscopic image of the region to be observed generated by an arbitrary way. According to this structure, it is advantageous in that the position of a light-emitting particle can be observed while being superimposed on a microscopic image of a region to be observed, for example, a microscopic image of a cell or a cell organelle, acquired by the other way. Also, in that case, when the size or the characteristics of a light-emitting particle are detectable, it is expected to more diverse information will be obtained by making it possible to refer to a characteristic of a light-emitting particle while being superimposed on a microscopic image of a cell or a cell organelle.

Furthermore, according to the "scanning molecule counting method", it is possible to count the number of light-emitting particles encompassed in the light detection region by counting the number of signals (the counting of particles) and acquire information about a concentration of the light-emitting particles. Accordingly, the signal processor in the present invention may be designed to determine the number of light-emitting particles in a region to be observed or the concentration of light-emitting particles in a liquid based on the number of the detected light-emitting particles. Also in this structure, it is advantageous in that the concentration of a light-emitting particle is observable together with a microscopic image of a region to be observed by another way.

The processes of the microscopic observation technique employing the way of the scanning molecule counting method in accordance with the above-mentioned inventive device are realizable with a general computer, also. Accordingly, in accordance with another manner of the present invention, there is provided a computer readable storage device having a computer program product including programmed instructions for observation with an optical microscope for detecting light from a light-emitting particle in a sample liquid to detect the light-emitting particle, using an optical system of a confocal microscope or a multiphoton microscope, said programmed instructions causing a computer to perform steps of: moving a position of a light detection region continuously multiple times within each observed subregion obtained by dividing a region to be observed within a field of view of the microscope into plural regions; detecting light from the light detection region by a light detector; and generating time series light intensity data of the light from the light detection region detected by the light detector while moving the position of the light detection region in each observed subregion, detecting a signal having a characteristic of a signal indicating light from each light-emitting particle individually in the time series light intensity data, and determining a position of each light-emitting particle corresponding to the detected signal in the region to be observed.

Also in this computer program, the moving of the position of the light detection region in each observed subregion may be conducted multiple times continuously in at least two directions and/or continuously in the same one direction for each observed subregion. The size of the observed subregion may be determined based on the size of the light detection region, and preferably, the size of the observed subregion may be set such that the moving length of the light-emitting particle to be detected within a time in which the position of the light detection region is moved in the observed subregion will be smaller than the size of the observed subregion. Further, in one embodiment, the length of one side edge of the observed subregion may be set to be almost equal to the diameter of the light detection region; one time of moving of the position of the light detection region in each observed subregion may be performed from when the front edge of the light detection region in its moving direction passes through one side edge of the observed subregion and until the rear edge of the light detection region in its moving direction reaches to the other side edge of the observed subregion. In this regard, preferably, the moving speed of the position of the light detection region is set higher than the diffusion moving velocity of the light-emitting particle.

Furthermore, also in the above-mentioned computer program, there may be comprised a procedure of generating a plot image obtained by plotting the position of the light-emitting particle whose the position in the region to be observed has been determined in a microscopic image of the region to be observed generated by an arbitrary way, and/or a procedure of determining information about the size of a light-emitting particle using a characteristic of a signal(s) of one same light-emitting particle obtained in the multiple times of moving of the light detection region in each observed subregion, where the characteristic of the signal(s) of the light-emitting particle used for the determination of the information about the size of the light-emitting particle may be, for example, an index value indicating a translational diffusional characteristic of the light-emitting particle or an index value indicating a rotational diffusion characteristic of the light-emitting particle. Moreover, the above-mentioned computer program may include a procedure of determining the number of light-emitting particles in the region to be observed or a concentration of the light-emitting particle in the liquid based on the number of the detected light-emitting particles.

Furthermore, according to the above-mentioned inventive device or computer program, there is realized a novel microscopic observation method employing the way of the scanning molecule counting method. Therefore, in accordance with yet other manner of the present invention, there is provided an optical microscopic observation method of detecting light from a light-emitting particle in a sample liquid to detect the light-emitting particle, using an optical system of a confocal microscope or a multiphoton microscope, comprising steps of: moving a position of a light detection region continuously multiple times within each observed subregion obtained by dividing a region to be observed within a field of view of the microscope into plural regions; detecting light from the light detection region by a light detector; and generating time series light intensity data of the light from the light detection region detected by the light detector while moving the position of the light detection region in each observed subregion, detecting a signal having a characteristic of a signal indicating light from each light-emitting particle individually in the time series light intensity data, and determining a position of each light-emitting particle corresponding to the detected signal in the region to be observed.

Also in this method, the moving of the position of the light detection region in each observed subregion may be conducted multiple times continuously in at least two directions and/or continuously in the same one direction for each observed subregion. The size of the observed subregion may be determined based on the size of the light detection region, and preferably, the size of the observed subregion may be set such that the moving length of the light-emitting particle to be detected within a time in which the position of the light detection region is moved in the observed subregion will be smaller than the size of the observed subregion. Further, in one embodiment, the length of one side edge of the observed subregion may be set to be almost equal to the diameter of the light detection region; one time of moving of the position of the light detection region in each observed subregion may be performed from when the front edge of the light detection region in its moving direction passes through one side edge of the observed subregion and until the rear edge of the light detection region in its moving direction reaches to the other side edge of the observed subregion. In this regard, preferably, the moving speed of the position of the light detection region is set higher than the diffusion moving velocity of the light-emitting particle.

Furthermore, also in the above-mentioned method, there may be comprised a step of generating a plot image obtained by plotting the position of the light-emitting particle whose the position in the region to be observed has been determined in the microscopic image of the region to be observed generated by an arbitrary way, and/or a step of determining information about the size of a light-emitting particle using a characteristic of a signal(s) of one same light-emitting particle obtained in the multiple times of moving of the light detection region in each observed subregion, where the characteristic of the signal(s) of the light-emitting particle used for the determination of the information about the size of the light-emitting particle may be, for example, an index value indicating a translational diffusional characteristic of the light-emitting particle or an index value indicating a rotational diffusion characteristic of the light-emitting particle. Moreover, the above-mentioned method may include a step of determining the number of light-emitting particles in the region to be observed or a concentration of the light-emitting particle in the liquid based on the number of the detected light-emitting particles.

Typically, the above-mentioned inventive microscopic observation technique is applied to observations, analyses, etc. of conditions of particulate, biological objects, e.g., biomolecules, such as protein, peptide, nucleic acid, lipid, sugar chain, amino acid or these aggregates, viruses, cells, etc., in liquid, such as in a cell or in a cell organelle, but the inventive technique may be used for analyses, etc. of conditions of non-biological particles (for example, atoms, molecules, micells, metal colloids, etc.) in an arbitrary liquid, and it should be understood that such cases belongs to the scope of the present invention, also.

Effect of Invention

Thus, according to the present invention, by employing the way of the scanning molecule counting method in the observation and analysis with a scan type optical microscope, it becomes possible to detect and observe individually a light-emitting particle which exists and moves in the inside of a thick sample liquid with more sufficient accuracy as compared with the prior art. Especially according to the inventive structure, sine the position of a detected light-emitting particle can be determined, it is possible to express the distribution of light-emitting particles as a two- or three-dimensional image, and thus, it is expected to acquire, from more multidirectional microscope observations and analyses thereof, diverse information and knowledges which have not been grasped in the past yet. Especially, in the structure of the present invention, since the existence distribution of light-emitting particles can be superimposed and observed on a microscopic image of a cell or a cell organelle, the present invention will be advantageously used for experiments for observing individually a behavior of an arbitrary particle in the inside of a cell or a cell organelle.

Other purposes and advantages of the present inventions will become clear by explanations of the following preferable embodiments of the present invention.

BRIEF DESCRIPTIONS OF DRAWINGS

FIG. 1A is a schematic diagram of the internal structure of an optical microscope device employing the scanning molecule counting method according to the present invention. FIG. 1B is a schematic diagram of a confocal volume (an observation region of a confocal microscope). FIG. 1C is a schematic diagram of the mechanism for changing the direction of the mirror 7 to move the position of a light detection region in a sample (cell). FIG. 1D is a schematic diagram of the mechanism for moving the horizontal position of a micro plate to move the position of the light detection region in a sample (cell).

FIGS. 2A and 2B are a schematic diagram explaining about the principle of the light detection in the scanning molecule counting method applied to the present invention, and a schematic diagram of a time variation of measured light intensity, respectively.

FIG. 3A is a schematic plan diagram of a region to be observed ObR and observed subregions OsR set in the field of view of a microscope. FIG. 3B is a schematic three-dimensional perspective diagram of a region to be observed and observed subregions. FIG. 3C is a schematic perspective diagram explaining about the manner of the moving of a light detection region which passes through an observed subregion.

FIGS. 4A and 4B are diagrams schematically showing examples of an observed subregion and a light detection region (upper rows) and time variations of light intensity (lower rows) when the observed subregion is scanned with the light detection region. FIG. 4C shows a schematic plan diagram illustrating the spatial relationship between an observed subregion and a light detection region and a drawing illustrating schematically an example of the time variation of light intensity for explaining about the principle of determining the position (coordinates) of a light-emitting particle in the observed subregion.

FIG. 5 is a drawing showing the detection procedure of a light-emitting particle in a microscopic observation method performed in accordance with the present invention in the form of a flow chart.

FIGS. 6A and 6B each are drawings of models in a case that a light-emitting particle crosses a light detection region owing to the Brownian motion and in a case that a light-emitting particle crosses a light detection region by moving the position of the light detection region in a sample solution at a velocity quicker than the diffusional moving velocity of the light-emitting particle. FIG. 6C shows drawings explaining an example of the signal processing step of the detected signals in the procedure for detecting the existence of a light-emitting particle from the measured time series light intensity data (time variation of photon count) in accordance with the scanning molecule counting method.

FIG. 8 shows examples of simulation results of schematic diagrams of observed subregions (8A, 8D); obtained time series light intensity data (8B, 8E); and integration data of light intensity data (8C, 8F) in a case of detecting the position of a light-emitting particle in accordance with the microscopic observation method in accordance with the present invention.

FIGS. 8A-8C show a case where a light detection region is moved in the X direction, and FIGS. 8D-8F show a case where a light detection region is moved in the Y direction.

EXPLANATIONS OF REFERENCE NUMERALS

Figure 2A:
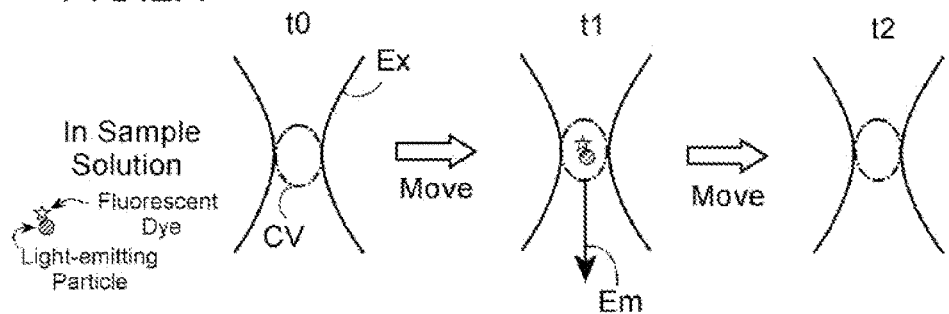

1—Confocal microscope
2—Light source
3—Single mode optical fiber
4—Collimating lens
5—Dichroic mirror
6, 7—Galvano mirror
8—Objective
9—Micro plate
10—Well (sample container)
11—Reflective mirror
12—Condenser lens
13—Pinhole
14—Barrier filter
14a—Dichroic mirror
15—Multi-mode optical fiber
16, 17—Mirror deflector
18—Photodetector
19—Stage position changing apparatus
20—Computer Description of Embodiments In the followings, preferable embodiments of the present invention are described in detail.

The Structure of a Microscope Device

In the basic structure, a microscope device which realizes the microscopic observation technique according to the present invention may be a device constructed by associating the optical system of a confocal microscope with a photodetector, enabling microscope observation with laser scanning as schematically illustrated in FIG. 1A. Referring to this drawing, the microscope device 1 consists of an optical system 2-18 and a computer 20 for acquiring and analyzing data together with controlling the operation of each part in the optical system. The optical system of the microscope device 1 may be the same as the optical system of a usual confocal microscope, where laser light, emitted from a light source 2 (Ex), forms a parallel beam with a collimator 2a, which beam is reflected on a dichroic mirror 5 and reflective mirrors (galvano mirror) 6 and 7, entering into an objective 8. Above the objective 8, typically, there is placed a sample container or a micro plate 9 having wells 10 arranged thereon, to which one to several tens of μL of a sample (a solution, cells, etc.) is dispensed, and the laser light emitted from the objective 8 is focused in the sample liquid in the sample container or well 10, forming a region having strong light intensity (excitation region). In the sample, when a light-emitting particle which is an object to be observed, typically, such as a fluorescent particle or a particle to which a light-emitting label, such as a fluorescent dye, is attached, enters into the excitation region, the light-emitting particle is excited and emits light during dwelling in the excitation region. The emitted light (Em) passes through the objective 8 and the dichroic mirror 5, and is reflected on the mirror 11 and condensed by a condenser lens 12, and then the light passes through the pinhole 13; transmits through the barrier filter 14 (where a light component only in a particular wavelength band is selected); and is introduced into a multimode fiber 15, reaching to the corresponding photodetector 18, and after the conversion into time series electric signals, the signals are inputted into the computer 20, where the processes of the detection of the signal of a light-emitting particle, the determination of the position of a light-emitting particle and/or other optical analyses are executed in manners explained later. In this regard, as known in ones skilled in the art, in the above-mentioned structure, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the excitation region is blocked. The focal region of the laser light illustrated in FIG. 1B is a light detection region, whose effective volume is usually about 1-10 fL in this microscope device (typically, the light intensity is spread in accordance with a Gaussian type distribution having the peak at the center of the region. The effective volume is a volume of an approximate ellipsoid bordering a surface where the light intensity is reduced to $1/e^2$ of the center light intensity), which focal region is called as "confocal volume". Furthermore, in the present invention, since the light from a single light-emitting particle, for example, the faint light from one fluorescent dye molecule, is detected, preferably, a super high sensitive photodetector, usable for the photon counting, is used for the photodetector 18. When the detection of light is performed by the photon counting, the measurement of light intensity is performed for a predetermined time in a manner of measuring the number of photons which have sequentially arrived at a photodetector in every measuring unit time (BIN TIME). Thus, in this case, the time series light intensity data is time series photon count data. Also, on the stage (not shown) of the microscope, there may be provided a stage position changing apparatus 19 for moving the horizontal position of the micro plate 9, in order to change the well 10 to be observed. The operation of the stage position changing apparatus 19 may be controlled by the computer 20. According to this structure, quick measurement can be achieved even when there are two or more specimens.

Furthermore, in the optical system of the above-mentioned microscope device, there is further provided a mechanism to scan the inside of the sample liquid with the light detection region, namely to move the position of the focal region i.e., the light detection region, within the sample solution. For this mechanism for moving the position of the light detection region, for example, there may be employed a galvano mirror device comprising reflective mirrors 6 and 7 and mirror deflectors 16 and 17 which change the directions of the mirrors 6 and 7, as schematically illustrated in FIG. 1A (the type of moving the absolute position of a light detection region). In this case, under control of the computer 20, the direction of the reflective mirrors 6 and 7 are changed as illustrated schematically in FIG. 1C so that the position of the light detection region will move, and thereby, for example, it becomes possible to scan the inside of a cell with the light detection region. In this regard, although the galvano mirror device may be the structurally same as that equipped in a usual laser scan type microscope, the manner of the moving of the position of the light detection region, i.e. the scanning way is different from the case of the usual laser scan type microscope as explained in detail later. Or, alternatively, as illustrated in FIG. 1D, the stage position changing apparatus 19 may be operated in order to move the horizontal position of the container 10 (micro plate 9), into which the sample liquid has been dispensed, to move the relative position of the light detection region in the inside of a cell in the sample (the type of moving the absolute position of a sample liquid). The driving of the position of the stage position changing apparatus 19 is performed by control of the computer 20. Further, although not illustrated, a mechanism in which the position of the light detection region is moved in the vertical direction in the sample liquid may be provided. For such a mechanism, concretely, a device which moves up and down on the objective 8 or the stage may be employed. Also, the moving of the position of a light detection region in the vertical direction is achievable by forming the beam light, which enters into and exits out of the back end of the objective, into a converging light or diverging light, instead of a parallel beam. Then, there may be constructed a mechanism that moves the position of the light detection region in the vertical direction by placing an offset lens having a variable focal length or a focus variable deformable mirror (not shown) on the optical path of the back end of the objective.

When a light-emitting particle to be an object to be observed emits light by multiphoton absorption, the above-mentioned optical system is used as a multiphoton microscope. In that case, since the light emission occurs only in the focal area of excitation light (light detection region), the pinhole 13 may be removed. Moreover, in the microscope device 1, there may be provided two or more excitation light sources 2, as shown in the drawing, where the wavelength of excitation light can be appropriately chosen, depending upon the excitation wave length of a light-emitting particle. Similarly, two or more photodetectors 18 may be provided, where, in a case that two or more kinds of light-emitting particle having different emission wavelengths are included in the sample, it may be designed that the light from these can be separately detected according to the wavelengths. Moreover, although not illustrated, there may be a polarizing beam splitter on the optical path so that polarized light components of detected light can be separately detected for detecting a polarization characteristic a light-emitting particle as in patent document 7.

The computer 20 has a CPU and a memory, and the inventive procedures are performed through the CPU executing various operational processings. In this regard, each procedure may be done with hardware. All or a part of processes explained in this embodiment may be performed by the computer 20 with a computer readable storage device having memorized the programs to realize those processes. Accordingly, the computer 20 may read out the program memorized in the storage device and realize the above-mentioned steps by performing the processing and calculations of information. Here, a computer readable storage device may be a magnetic disk, a magnetic optical disk, a CD-ROM, a DVD-ROM, a semiconductor memory, etc. Furthermore, the above-mentioned program may be distributed to a computer through communication line, and the computer which has received this distribution may be made to execute the program.

The Principle of Inventive Microscopic Observation Technique

As described in the column of "Summary of Invention", in the inventive microscopic observation technique, briefly, in the observation with a scan type optical microscope, a region to be observed is divided into plural observed subregions; each observed subregion is scanned multiple times one by one in the way of the scanning molecule counting method; and the presence or absence of a light-emitting particle and its position are determined. Then, because the position of a light-emitting particle within a region to be observed is determined, it becomes possible to express the existence distribution of light-emitting particles as an image (imaging the existence distribution of light-emitting particles). In the followings, the principles of the scanning molecule counting method and the inventive microscopic observation technique will be explained.

1. Principle of Scanning Molecule Counting Method

Figure 2B:
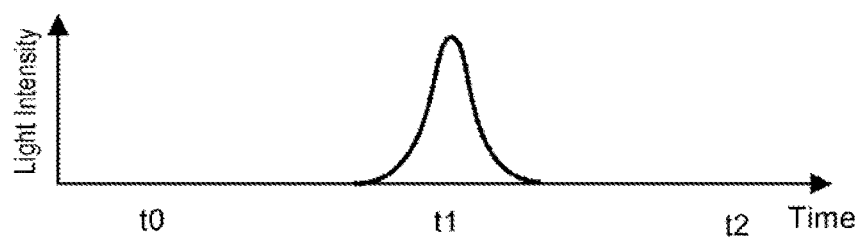

In the scanning molecule counting method (patent documents 3-8), basically, the light detection is performed together with moving the position of a light detection region CV in a sample, namely, scanning the inside of the sample solution with the light detection region CV by driving the mechanism (mirror deflector 17) for moving the position of the light detection region to change the optical path or by moving the horizontal position of the container 10 (micro plate 9) into which the sample liquid is dispensed, as schematically drawn in FIG. 2A. Then, for example, during the moving of the light detection region CV (in the drawing, time to-t2), when the light detection region CV passes through a region where one light-emitting particle exists (t1), light is emitted from the light-emitting particle, and a pulse form signal having significant light intensity (Em) appears on time series light intensity data as drawn in FIG. 2B. Thus, by detecting, one by one, each pulse form signal (a significant light intensity variation) appearing as illustrated in FIG. 2B during the execution of the moving of the position of the light detection region CV and the light detection as described above, the light-emitting particles are detected individually, and by counting the number thereof, the information about the number, concentration or number density of the light-emitting particles existing in the measured region can be acquired. In the principle of this scanning molecule counting method, no statistical operation processing, like computation of fluctuation of fluorescence intensity, is performed, and light-emitting particles are detected one by one, and therefore, even for a sample in which the concentration of a particle to be observed is too low to conduct an analysis with sufficient accuracy through fluorescence correlation spectroscopy (FCS) and fluorescence intensity distribution analysis (FIDA), the information about the concentration or the number density of the particles is acquirable. Examples of concrete ways of detecting the signal of a light-emitting particle from time series light intensity data will be mentioned later.

2. Principle of Inventive Microscopic Observation Technique (i) Overview

Figure 9A:
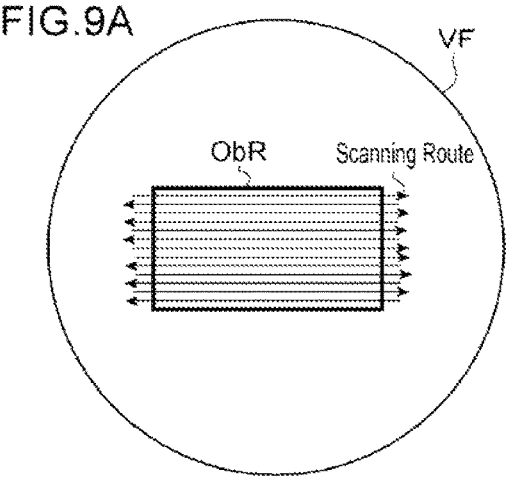
FIG. 9A is a drawing showing schematically an example of a scanning pattern in a raster scan mode in a conventional laser scan type light microscope.
Figure 9B:
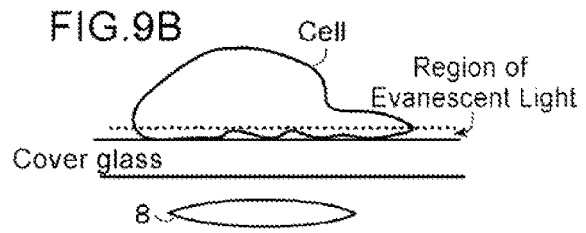
FIG. 9B is a schematic drawing explaining about the observable area in a microscope using evanescent light.

As described in the column of "Summary of Invention", in the case of a usual laser scan type confocal microscope device, the scanning of a light detection region CV in a region to be observed ObR is performed in a raster scan mode, typically, as schematically drawn on FIG. 9A, and thus, the position of the light detection region CV is moved successively over the whole area of the region to be observed ObR. The position of the region to be observed, i.e., a scan size, can be set to an arbitrary position in the field of view VF and an arbitrary height in the direction of the optical axis in the range where the influence of the aberration of light is allowable. And, when integration of light intensity is carried out, for instance, when the detected light intensity is weak, the light detection region CV is repeatedly moved along the same scanning route. However, in the case of this structure, if the position of a light-emitting particle detected in the first scan would have moved in the second or later scan, the significant effect of the integration of light intensity could not be obtained. On the other hand, in the case of a microscope device using evanescent light, instead of detecting light by the scanning of a micro light detection region CV, it is possible to take an image in a field of view or a region to be observed into a photodetector, such as a camera, at once, and in that case, in the photodetector, such as a camera, the integration of light intensity or light amount is continuously possible, and therefore, the significant effect of the integration of light intensity will be obtained also in a case of the image of a light-emitting particle whose position changes. However, in the case of the microscope device using evanescent light, as schematically drawn in FIG. 9B, the observable area will be limited to the region near the cover glass surface to which the evanescent light reaches in a sample.

Figure 3A:
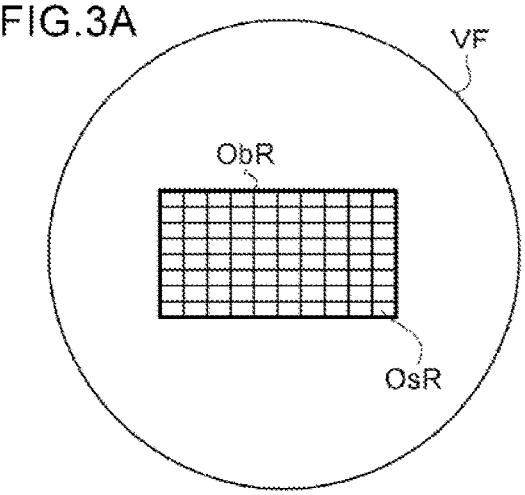
Figure 3B:
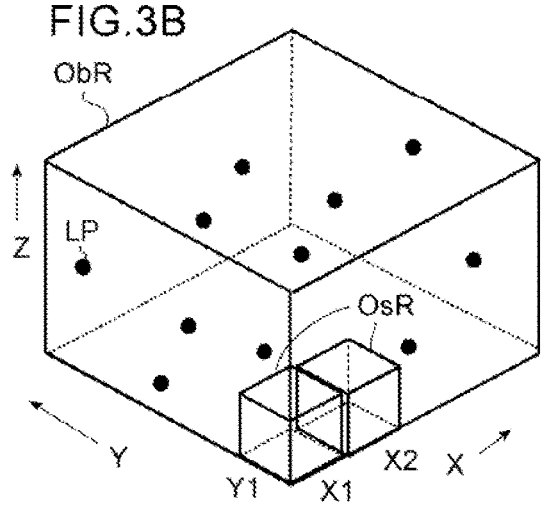
Figure 3C:
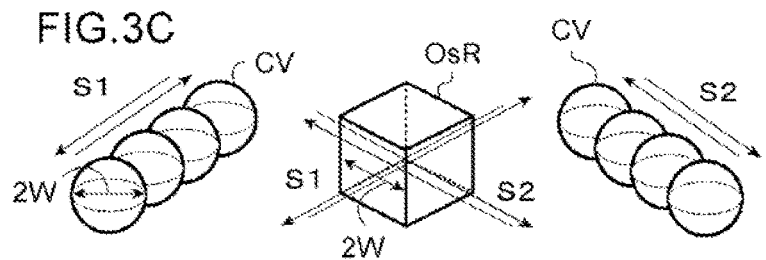

Then, in the present invention, in order to enable detecting a light-emitting particle whose position changes in much broader regions, in a structure of a scan type optical microscope device of the type in which the position of a light detection region of a confocal microscope or a multiphoton microscope moves, a region to be observed ObR within a field of view VF is (virtually) divided into plural observed subregions OsR as schematically drawn in FIG. 3A or 3B, and in each observed subregion, for example, in each of regions (X1, Y1), (X2, Y1), . . . , as shown in FIG. 3B, the scanning with the light detection region is performed multiple times. In the multiple times of scanning, the position of the light detection region may be moved in at least two mutually different directions, for example, with reference to FIGS. 3B and 3C, at least one time in each of the X direction S1 and the Y direction S2, or at least one time in each of the X direction S1, the Y direction S2 and the Z direction (not shown), and during the scanning, measurement of light intensity from the light detection region may be carried out. Also, in the multiple times of scanning, the position of the light detection region may be moved in one direction, for example, at least two times in the X direction S1 or Y direction S2, and during the scanning, measurement of light intensity from the light detection region may be carried out. Then, in the light intensity data from the light detection region obtained in time series during the multiple times of scanning with the light detection region, the detection of the signal of a light-emitting particle is performed in the way of the scanning molecule counting method explained briefly previously.

In the above-mentioned microscopic observation technique according to the present invention, the moving range of the position of the light detection region can be arbitrarily set in the range where the influence of the aberration of light is allowable as in the case of a usual laser scan type confocal microscope device, and thus, there are no limitations in the observable region as in the cases of microscope devices using evanescent light. Further, the time length taken for scanning with the light detection region multiple times in each observed subregion is largely shorter as compared with a raster scan mode of a usual laser scan type confocal microscope device, and thus, the detection and locating of a light-emitting particle moving in a sample, such as a light-emitting particle moving in a cell or a cell organelle can be achieved with more sufficient accuracy. Especially, in a case that the emitted light of a light-emitting particle is weak, and thus, the integration of light intensity will become effective for detecting it significantly, the scanning time of each observed subregion can be set enough short to make it possible to detect the light of the same light-emitting particle almost at the same position by setting appropriately the relation between the size of an observed subregion and a scanning speed, and thereby, a significant integration effect is expected. Furthermore, the detection of a light-emitting particle is carried out in accordance with the principle of the scanning molecule counting method, where no statistical operation processing like the computation of fluorescence intensity fluctuation is performed, and therefore, the detection of the existence of a particle and the acquisition of information about a concentration or number density of particles are achievable even for a sample in which the concentration of particles to be observed is too low to conduct analyses with sufficient accuracy in FCS (Fluorescence Correlation Spectroscopy), FIDA (Fluorescence Intensity Distribution Analysis), etc.

(ii) Setting of the Size of Observed Subregion and the Moving Range of Light Detection Region As described in the column of "Summary of Invention", the time taken for a light detection region to scan an observed subregion is determined with the size of an observed subregion, and thus, typically, the size of an observed subregion is determined based on the size of the light detection region. In this respect, if the size of an observed subregion is larger than the size of a light detection region, the whole region of the observed subregion cannot be covered by one time of the light detection region passaging through the observed subregion, and in that case, it would be necessary to make the light detection region pass through the observed subregion again while including the portion which has not been included in the light detection region in the first passage in the observed subregion, and thereby, to do this, the scanning time would be extended. Therefore, with respect to the size of an observed subregion, preferably, as schematically drawn in FIG. 3C and FIG. 4A-4C, its one side edge length is set to be equal to the diameter 2W of the light detection region. In this regard, although the shape of an observed subregion is formed to be a cube preferably, it should be understood that the observed subregion may be a rectangular parallelepiped extending longer in the scanning direction of the light detection region (especially, when the scanning is performed only in one direction).

Figure 4A:
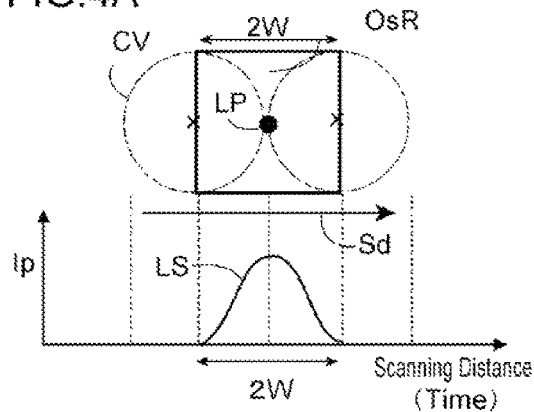
Figure 4B:
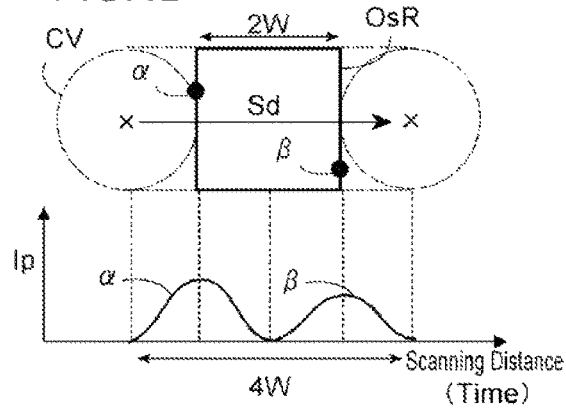
Figure 4C:
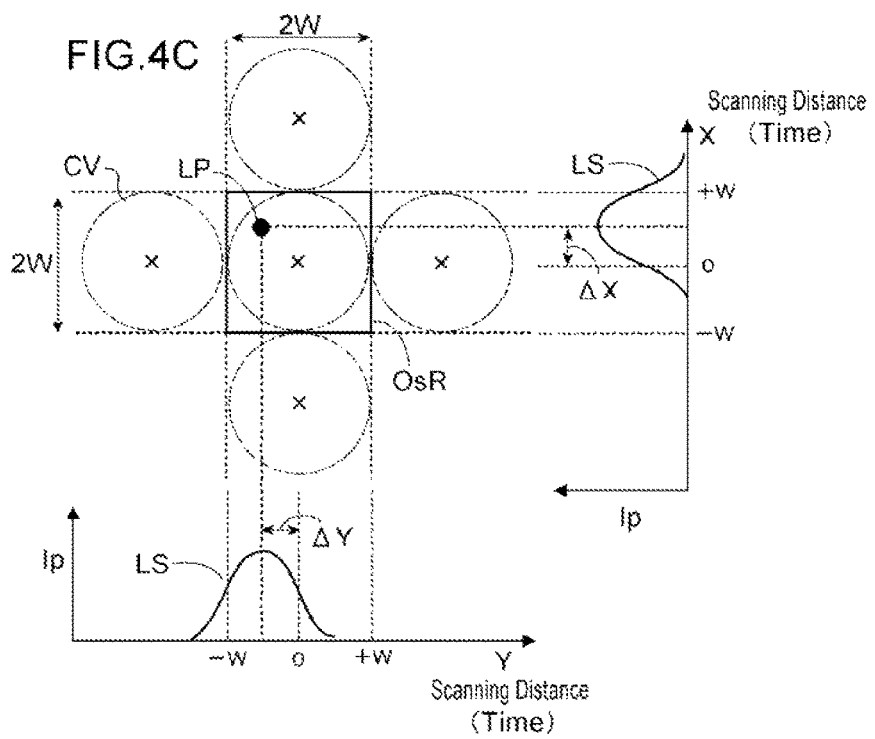

Moreover, preferably the moving range of the light detection region in each observed subregion is set such that the light detection region moves in one time scanning from the position at which the front edge of the light detection region CV in its moving direction Sd touches one side edge of the observed subregion OsR from its outside to the position at which the rear edge of the light detection region CV touches the opposite side edge of the observed subregion OsR from its outside as schematically drawn in FIGS. 4A and 4B. In measurement with a confocal microscope or a multiphoton microscope, the total amount of the light from the region included in a light detection region is measured as one data value, where the detected light intensity of a light-emitting particle changes depending upon the position of the light-emitting particle in the inside of the light detection region. Namely, usually, the light intensity of a light-emitting particle in the light detection region becomes its highest when the light-emitting particle is at the almost center of the light detection region and decreases as the light-emitting particle moves toward the edge of the light detection region. This spread of the distribution of the light intensity of the light-emitting particle in the light detection region corresponds to the size of the light detection region, and follows a point spread function (PSF) determined with the numerical aperture of the objective, the incident beam diameter of excitation light to the objective, the diameter of a pinhole, etc. Accordingly, when a light detection region passes through the existence position of a light-emitting particle as already explained in conjunction with FIG. 2, the light intensity of the light-emitting particle will change in a bell-shaped pulse form. In the scanning molecule counting method, such a pulse form time variation of light intensity is detected as a signal of a single light-emitting particle. Namely, also in the inventive microscopic observation technique, as drawn in FIG. 4A, in order to detect the signal of one light-emitting particle LP with sufficient accuracy, it is preferable to make the light-emitting particle pass from one edge of the light detection region to its other edge so that a bell-shaped pulse form time variation LS of the light intensity (the width from one skirt edge to the other skirt edge becomes the diameter 2W of the light detection region) will be obtained. On the other hand, as drawn in FIG. 4B, in a case of light-emitting particles α and β existing near the periphery of the observed subregion OsR, the bell-shaped pulse form time variations α and β of the light intensity can be detected, respectively, by moving the light detection region CV from the position at which one edge of the light detection region CV touches one side edge of the observed subregion OsR (the left-hand side position) to the position at which the other edge of the light detection region CV touches the opposite side edge of the observed subregion OsR (the right-hand side position) as shown in the drawings. Therefore, as noted above, the moving range of a light detection region in each observed subregion is preferably the range where the front edge and rear edge of a light detection region in its moving direction touch side edges of an observed subregion from its outside, respectively, as in FIG. 4B. That is, the moving length of a light detection region for one observed subregion is set to 4W, i.e. twice of the diameter of the light detection region.

(iii) Determination of the Position of a Light-Emitting Particle

As noted above, when the detection process of a light-emitting particle is performed for each observed subregion, the position of the observed subregion within a region to be observed is beforehand known at the time of the setting of the observed subregion, and therefore, the position of a light-emitting particle detected in each observed subregion will be determined at the resolution of the size of the observed subregion. Furthermore, as noted, in a case that the detection of the signal of a light-emitting particle in each observed subregion is carried out by the detection of a bell-shaped pulse form time variation of the light intensity (a signal of a light-emitting particle), the position (the time point) of the peak of the signal of a light-emitting particle is specified on time series light intensity data. Since a light-emitting particle is considered to exist on the center axis of the light detection region in the direction perpendicular to its moving direction at the position of the peak of the signal of the light-emitting particle, the position of a light-emitting particle in an observed subregion can also be determined by detecting the position of the peak of the signal of the light-emitting particle. Concretely, as schematically drawn in FIG. 4C, in time series light intensity data during scanning with a light detection region in the X direction, when the position of the peak of the signal of a light-emitting particle is determined, the coordinate in the X direction of the light-emitting particle is determined from a gap ΔX of the peak position from the center position (which may be the side edge position) of an observed subregion. Similarly, in time series light intensity data during scanning with a light detection region in the Y direction, when the position of the peak of the signal of a light-emitting particle is determined, the coordinate in the Y direction of the light-emitting particle is determined from a gap ΔY of the peak position from the center position (which may be the side edge position) of an observed subregion. Then, the position of the light-emitting particle within a region to be observed will be determined with the position coordinates of the observed subregion, and ΔX and ΔY. (Although not illustrated, also in the Z direction, the coordinate in the Z direction of a light-emitting particle may be determined by a gap ΔZ of the peak position from a specific position of an observed subregion.)

Processing Operation Step of Microscopic Observation

Figure 5:
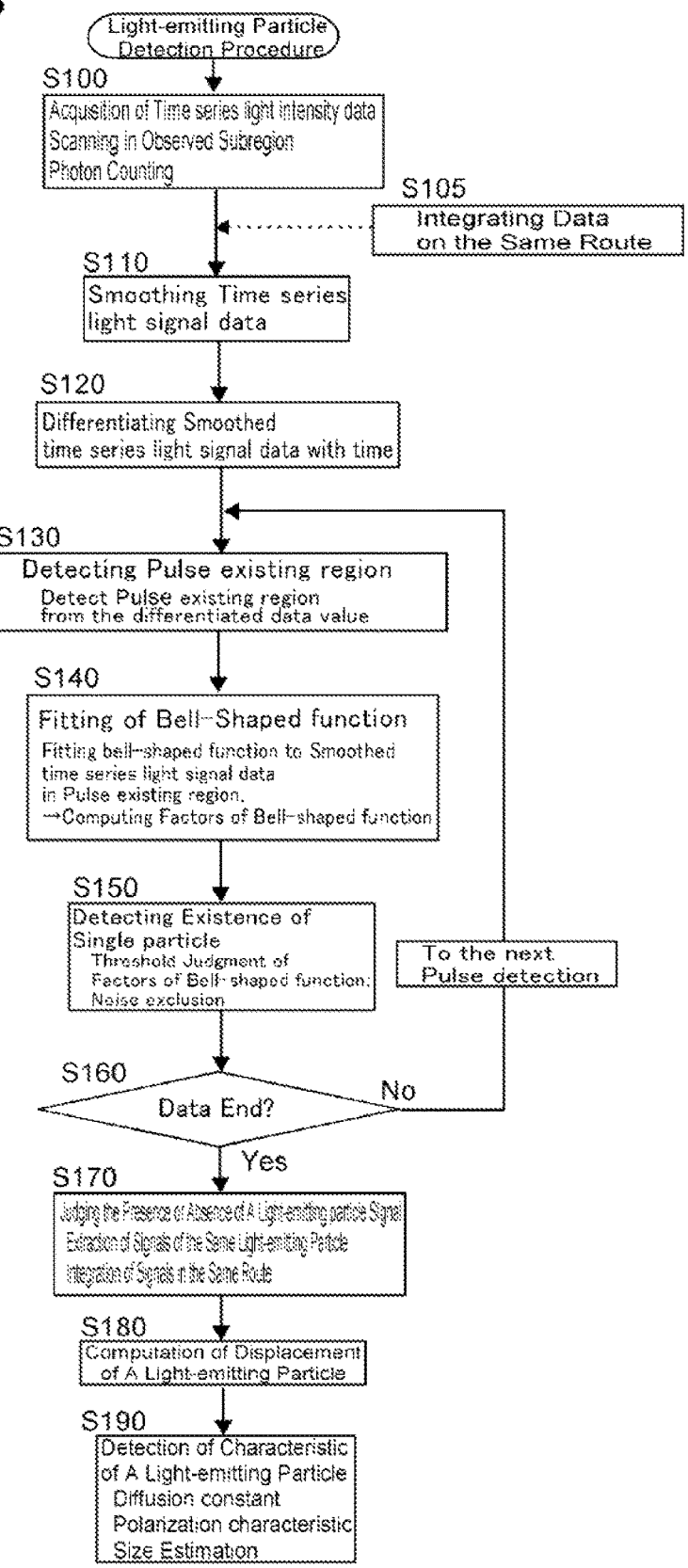

In an embodiment of a microscope observation according to the present invention using the microscope device 1 illustrated in FIG. 1A, concretely, there are performed (1) the preparation of a sample containing light-emitting particles; (2) a process of measuring light intensity of the sample and (3) a process of analyzing the measured light intensity. FIG. 5 shows processes in this embodiment in the form of flow chart.

(1) Preparation of a Sample

The particle to be an observed object in the inventive microscopic observation technique may be an arbitrary particle as long as it exists in an arbitrary liquid and it may be a biological molecule, i.e. a protein, a peptide, a nucleic acid, a lipid, a sugar chain, an amino acid, etc. or an aggregate thereof, a virus, a cell, a metallic colloid or other non-biological molecules. When the particle to be an observed object is not a particle which emits no light, there is used a particle obtained by attaching a light emitting label (a fluorescence molecule, a phosphorescence molecule, and a chemiluminescent or bioluminescent molecule) to the particle to be the observed object in an arbitrary manner. Typically, the sample is an aqueous solution, but not limited to this, and it may be an organic solvent or other arbitrary liquids. Further, the particle to be an observed object may be a particle which exists and moves (changes its position) owing to diffusion or any other reasons in a cell or a cell organelle. Namely, the sample may be a sample liquid used for a usual microscopic observation of a cell or a cell organelle.

(2) Measurement of Light Intensity of a Sample Liquid (FIG. 5—Step 100)

In the microscope observation of this embodiment, as noted above, measurement of light intensity is performed together with the moving of the position of a light detection region in each observed subregion in a region to be observed. The moving of the position of the light detection region is made by driving the galvano mirror devices 16 and 17 or the stage position changing apparatus 19. In the operation processes, typically, after dispensing a sample into the well(s) 10 of the micro plate 9 and putting it on the stage of the microscope, when a user inputs to the computer 20 a command of starting a measurement, the computer 20 executes programs memorized in a storage device (not shown) (the process of moving the position of the light detection region in the sample, and the process of detecting light from the light detection region during the moving of the position of the light detection region) to start radiating the excitation light and measuring the light intensity in the light detection region in the sample. During this measurement, under the control of the operation process of the computer 20 according to the programs, the galvano mirror devices 16, 17 or the stage position changing apparatus 19 drives the galvanomirrors 6, 7 or the micro plate 9 on the stage of the microscope to move the position of the light detection region in the well 10, and simultaneously with this, the photodetector 18 sequentially converts the detected light into electric signals and transmits them to the computer 20, which generates the time series light intensity data from the transmitted signals and stores them in an arbitrary manner. In this regard, the photodetector 18 is typically a super high sensitive photodetector which can detect an arrival of a single photon, and thus when the detection of light is performed by the photon counting, the time series light intensity data may be time series photon count data.

As noted, the scanning in the region to be observed with a light detection region is performed by each observed subregion. Concretely, for example, the moving of the light detection region may be carried out in each observed subregion (a) at least 1 time in each of the X direction and Y direction; (b) at least 1 time in each of the X direction, Y direction and Z direction, (c) at least 1 time in each of the X direction (or Y direction) and the Z direction, or (d) at least 2 times in each of the X direction, Y direction, Z direction. And when the scanning for one observed subregion is completed, the moving of a light detection region may be similarly carried out in an adjoining observed subregion.

The moving speed of the position of the light detection region during the light intensity measurement may be a predetermined speed set arbitrarily, e.g. experimentally or so as to meet with an analytic purpose. The interpretation of a measurement result becomes easier when the lapsed time during the measurement and the moving length of the position of the light detection region are proportional to one another, and thus, basically, it is preferable that the moving speed is constant, but not limited thereto.

Figure 6A:
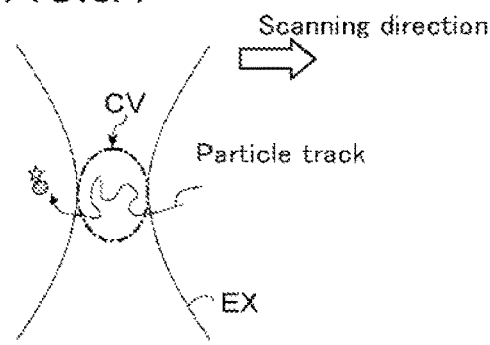

By the way, with respect to the moving speed of the position of the light detection region, in order to perform individual detection of light-emitting particles from the measured time series light intensity data or the counting of the number of light-emitting particles quantitatively with sufficient accuracy, it is preferable to set the moving speed to a value quicker than the moving speed in the random motion of a light-emitting particle, i.e., the Brownian motion. Since a particle to be observed in the inventive microscopic observation technique is a particle which can move in liquid, its position may move with time progress according to the Brownian motion. And if the moving speed of the position of a light detection region is slower than the moving of a particle according to the Brownian motion, as schematically drawn in FIG. 6A, the particle moves at random in the region, and thereby, its light intensity changes at random (As already noted, the excitation light intensity in the light detection region has the peak at the center of the region and reduces toward the outside), so that it becomes difficult to specify a significant light intensity variation corresponding to each light-emitting particle. Thus, preferably, the moving speed of the position of the light detection region is set quicker than the average moving speed of particles by the Brownian motion (diffusion moving velocity) so that a particle will pass through the light detection region in an approximately straight line as drawn in FIG. 6B, and thereby the profile of a light intensity variation corresponding to each light-emitting particle will form a bell-shaped profile, as illustrated in the most upper row of FIG. 6C (When a light-emitting particle passes through the light detection region in an approximately straight line, the profile of the light intensity variation will be almost the same as the excitation light intensity distribution), and it can become easier to determine the correspondence of each light-emitting particle to the light intensity.

Concretely, the time $\Delta t$ required for a light-emitting particle having a diffusion coefficient D to pass through the light detection region of radius W (confocal volume) by the Brownian motion is given from the equation of the relation of mean-square displacement:

$$(2W)^2 = 6D \cdot \Delta t \qquad (1)$$

as:

$$\Delta t = (2W)^2/6D \qquad (2),$$

and thus, the velocity of the light-emitting particle moving by the Brownian motion (diffusional moving velocity) Vdif, becomes approximately $$V\text{dif} = 2W/\Delta t = 3D/W \qquad (3)$$

Then, with reference to this, the moving speed of the position of the light detection region may be set to a value sufficiently quicker than Vdif. For example, when the diffusion coefficient of a light-emitting particle is expected to be about $D=2.0\times10^{-10}$ m$^2$/s, Vdif will be $1.0\times10^{-3}$ m/s, supposing W is about 0.62 μm, and therefore, the moving speed of the position of the light detection region may be set to its 10 times or more, 15 mm/s, etc. In this regard, when the diffusion coefficient of a particle to be observed is unknown, an appropriate moving speed of the position of the light detection region may be determined by repeating the executions of a preliminary experiment with setting various moving speeds of the position of the light detection region in order to find the condition that the profile of the light intensity variation becomes an expected profile (typically, similar to the excitation light intensity distribution).

Furthermore, in a case that the scanning of the light detection region is performed multiple times in each observed subregion, if a light-emitting particle which exists in an observed subregion in the scanning time is not kept from deviating from the observed subregion, no significant integration effect would be obtained, and also, as explained later, any analyses using the change of the position of a light-emitting particle within a scanning time (detection of a diffusing constant, etc.) cannot be performed effectively. Thus, it is preferable that the size of an observed subregion is set so that the (expected) moving length of a light-emitting particle to be detected within a time in which the position of the light detection region is moved in an observed subregion will be smaller than the size of an observed subregion. However, as noted above, preferably, one side edge length of an observed subregion is to be set to almost equal to the diameter of the light detection region. Then, in practical, the scanning speed may be set to give the scanning time in which the moving length of a light-emitting particle by its diffusion will not exceed beyond the size of the observed subregion. Concretely, the scanning time $\Delta T$ of a light detection region in k times of scanning a route, whose length in one time scanning is 4W, at the moving speed v is given by:

$$\Delta T = 4W \cdot k/v \qquad (4)$$

On the other hand, the moving length x of the light-emitting particle by diffusion in the scanning time $\Delta T$ is given, similarly to Exp. (1) by:

$$\langle x \rangle^2 = 2D\Delta T \qquad (5)$$

Here, the conditions of $x^2 \leq W^2$ should be established, and thus, it is preferable that the scanning speed is set so that $$v \leq 8D \cdot k/W \qquad (6)$$

will be established.

(3) Analysis Processing of Light Intensity

When the time series light intensity data is generated through the scanning of each observed subregion, there may be carried out the detection of a signal of a light-emitting particle, the counting of light-emitting particles, the determination of the position of a light-emitting particle, and other various analyses (concentration calculation etc.), using the light intensity values of the time series light intensity data, as described below (i) Individual Detection of Signal of Light-Emitting Particles (FIG. 5—Steps 110-160)

Figure 6B:
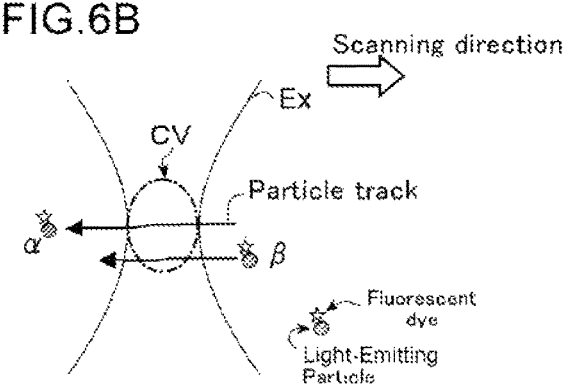

As already noted, when the track of one light-emitting particle in its passing through the light detection region is approximately straight as shown in FIG. 6B, the light intensity variation in the signal corresponding to the particle on the time series light intensity data has a bell shaped profile reflecting the light intensity distribution in the light detection region determined by the optical system. Thus, basically in the scanning molecule counting method, when the time width $\Delta \tau$ for which the light intensity value exceeding an appropriately set threshold value Ith continues is in a predetermined range on the light intensity data, the signal having the profile of the light intensity may be judged to correspond to one particle having passed through the light detection region, and thereby one light-emitting particle is detected. And a signal whose light intensity does not exceed the threshold value Ith or which does not have time width $\Delta \tau$ in the predetermined range is judged as noise or a signal of a contaminant. Further, when the light intensity distribution in the light detection region can be assumed as Gaussian distribution:

$$I = A \cdot \exp(-2t^2/a^2) \qquad (7),$$

and when the intensity A and the width a, computed by fitting Expression (7) to the profile of a significant light intensity (a profile which can be clearly judged not to be a background), are within the respective predetermined ranges, the profile of the light intensity may be judged to correspond to one particle having passed through the light detection region, and thereby the detection of one light-emitting particle will be done (The signal with the intensity A and the width a out of the predetermined ranges may be judged as a noise or a contaminant signal and ignored in the later analysis, etc.).

Figure 6C:
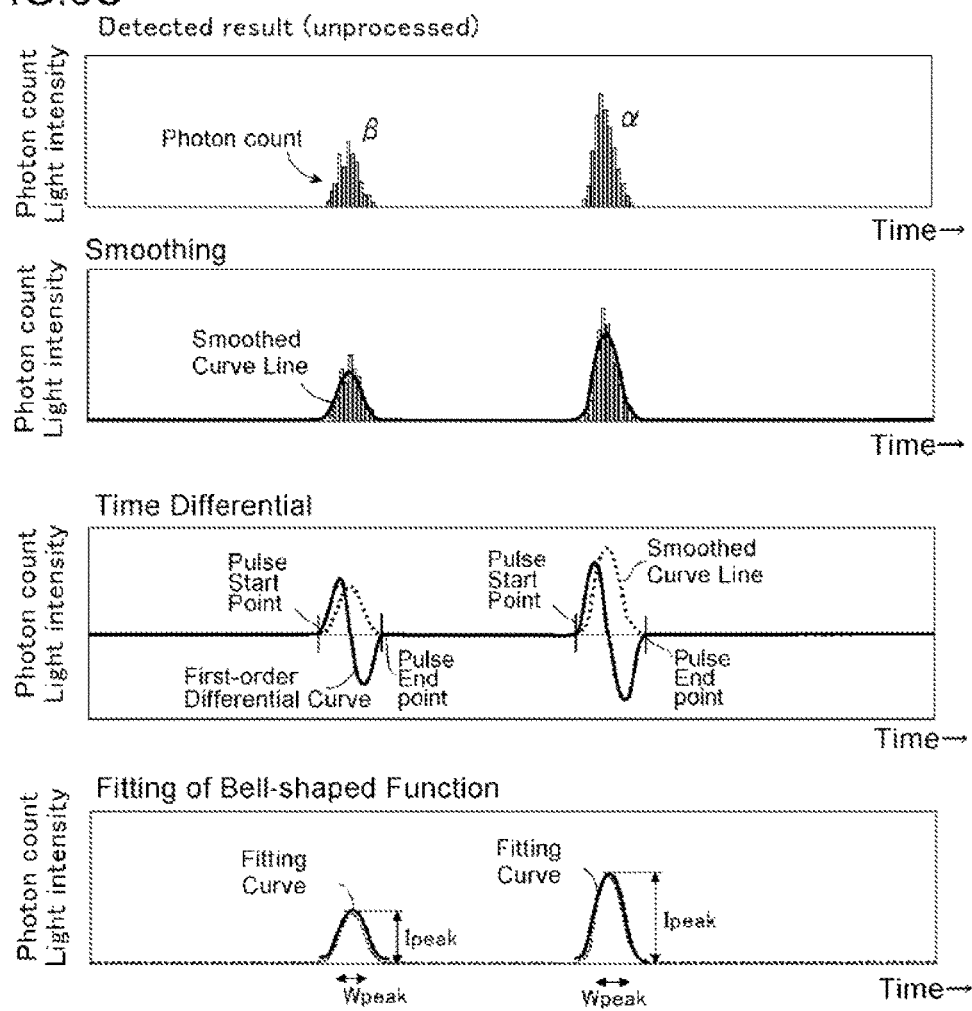

As an example of the process of the detection of signals on light intensity data, first, a smoothing treatment is performed to the time series light signal data (FIG. 6C, the most upper row "detected result (unprocessed)") (FIG. 5—step 110, FIG. 6C mid-upper row "smoothing"). Although the light emitted by a light-emitting particle is stochastic so that gaps will be generated in data values in minute time, such gaps in the data value can be disregarded by the smoothing treatment. The smoothing treatment may be done until the gaps in the data value as mentioned can be disregarded, for example, by the moving average method. In this regard, parameters in performing the smoothing treatment, e.g., the number of datum points in one time of the averaging, the number of times of a moving average, etc. in the moving averages method, may be appropriately set in accordance with the moving speed (scanning speed) of the position of the light detection region and/or BIN TIME in the light intensity data acquisition.

Next, on the light intensity data after the smoothing treatment, in order to detect a time domain (pulse existing region) in which a significant pulse form signal (referred to as "pulse signal" hereafter) exists, the first differentiation value with time of the light intensity data after the smoothing treatment is computed (step 120). As illustrated in FIG. 6C, the mid-low row "time differential", in the time differential value of light signal data, the variation of the value increases at the time of the signal value change, and thereby, the start point and the end point of a significant signal can be determined advantageously by referring to the time differential value.

Figure 7:
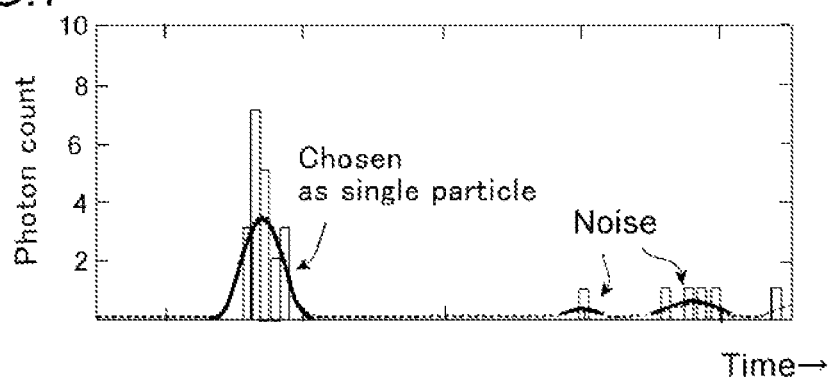
FIG. 7 shows examples of measured photon count data (bar graph); curves obtained by carrying out the smoothing of the data (dotted line); and Gauss functions fitted on the pulse existing region (solid line). In the drawing, the signals attached with "noise" are disregarded as signals due to noises or a contaminant.

After that, a significant pulse signal is detected sequentially on the light intensity data (Steps 130-160). Concretely, first, on the time-differential value data of the light intensity data, the start point and the end point of one pulse signal are searched and determined by referring to the time differential value sequentially, so that a pulse existing region will be specified (step 130). When one pulse existing region has been specified, the fitting of a bell-shaped function is applied to the smoothed light intensity data in the pulse existing region (FIG. 6C, the lower row "bell-shaped function fitting"), and then, parameters of the pulse of the bell-shaped function, such as the peak intensity (the maximum), Ipeak; the pulse width (full width at half maximum), Wpeak; the correlation coefficient in the fitting (of the least square method), etc. are computed (step 140). In this regard, although the bell-shaped function to be used in the fitting is typically Gauss function, it may be Lorentz type function. And, it is judged whether or not computed parameters of the bell shaped function are in the corresponding predetermined ranges assumed for the parameters of a bell shaped profile drawn by a pulse signal detected when one light-emitting particle passes through the light detection region, namely, whether or not the peak intensity, pulse width and correlation coefficient are in the corresponding predetermined ranges, respectively (step 150). Accordingly, as shown in FIG. 7 left, the signal, whose computed parameters of the bell-shaped function are judged to be within the ranges assumed in a signal corresponding to one light-emitting particle, is judged as a signal corresponding to one light-emitting particle, and thereby one light-emitting particle is detected. On the other hand, a pulse signal, whose computed parameters of the bell-shaped function are not within the assumed ranges, as shown in FIG. 7 right, is disregarded as noise. In this regard, simultaneously with detection of signal(s) of (a) light-emitting particle(s), the counting of the number of signals, i.e., the counting of light-emitting particles, may be performed.

The searching and the judgment of a pulse signal in the above-mentioned processes of steps 130-150 may be repetitively carried out in the whole regions of the light intensity data of each observed subregion (step 160). In a case that mutually different components of the light are detected separately and two or more time series light intensity data are generated, the processes of steps 130-150 may be performed for each time series light intensity data. In this regard, the process of detecting a signal of a light-emitting particle from light intensity data individually may be performed by an arbitrary way, other than the above-mentioned processes.

(ii) Integration of Signals of the Same Light-Emitting Particle (FIG. 5—Step 170)

By the way, in the microscopic observation technique of this embodiment, when the scanning in the same direction is performed multiple times for each observed subregion, it is expected that signals of the same light-emitting particle have appeared repeatedly on time series light detection data. In that case, the improvement in the accuracy of the signal of a light-emitting particle is expected by integrating the data values on time series light detection data or the data values of the regions detected as a signal of a light-emitting particle along the scanning route while the positions on the scanning route in the data values will be in agreement with one another. In one of concrete manners of such a integration, as noted, after detecting individually signals of light-emitting particles on time series light detection data in each observed subregion, the light intensity values of the signals of a detected light-emitting particle are integrated, and their total value or average value may be used as the light intensity value of the signal of the light-emitting particle. The processes for extracting the signals of the same light-emitting particle in the case of the integration of light intensity values may be performed, for example, in the way described in patent documents 6-7.

For an alternative manner of the integration of time series light detection data, the integration of data values along the scanning route may be carried out prior to the individual detection of signals of light-emitting particles on the time series light detection data (step 105). In this case, especially when the light intensity value of a light-emitting particle obtained in one time scanning is weak, the light intensity value for the light-emitting particle increases by integration of the data values, and thereby, improvement in the accuracy of the individual detection of the signal of a light-emitting particle is expected. FIG. 8 is diagrams showing the simulation examples of processes in the cases of performing individual detection of a signal of a light-emitting particle after the integration of data values along a scanning route. In this regard, FIGS. 8A and 8D each are drawings schematically showing the motion of a light-emitting particle LP with a diffusing constant D=1 $\mu m^2$/sec in a condition that the light-emitting particle moves by the Brownian motion within the observed subregion OsR of 0.4 μm square while a light detection region CV repetitively moves at 6.4 mm/sec in speed (0.8 μm in amplitude, 4 kHz in frequency) in the X direction (S1+, S1− in FIG. 8A) and in the Y direction (S2+, S2− in FIG. 8D); and FIG. 8B, the upper row, and FIG. 8E, the upper row, are examples of photon counts PC obtained in the scanning. In the cases of these examples, the scanning time in scanning five times will be 1.25 msec, and thus, the displacement by diffusion becomes about 0.09 μm.

With reference to FIG. 8, as understood from FIG. 8B upper row and FIG. 8E upper row, as noted above, when photon detection is performed during scanning, the signal of the same light-emitting particle LP appear repeatedly in time series photon count data PC (light intensity data). However, in the illustrated examples, the moving direction of the light detection region turns to be reverse in scanning in each even-numbered time. Thus, before the integration of data, reversing the time axis is performed for the data area corresponding to the periods in which the moving direction of the light detection region was reversed as shown in FIG. 8B lower row, and FIG. 8E lower row. After this, in the time series photon count data of FIG. 8B lower row, and FIG. 8E lower row, the integration of data values is performed under the condition that the position on the scanning route is to be matched, namely, the regions corresponding to the respective arrows in FIG. 8B lower row, and FIG. 8E lower row will be overlapped mutually. Then, as illustrated in FIGS. 8C and 8F, since the signal intensity of a light-emitting particle LP increases, an improvement in the accuracy of individual detection of the signal of a light-emitting particle (the accuracy in discriminating between a signal and a noise) will be expected. In this regard, in time series photon count data of each observed subregion, the concrete process for improving the accuracy of the signal detection of a light-emitting particle may be performed in the way described in patent document 8.

(iii) Determination of Position of Light-Emitting Particle (FIG. 5—Step 180)

As already noted, when the signal of a light-emitting particle is detected in each observed subregion, since the position (coordinates) of each observed subregion OsR in the region to be observed ObR is known, the position of the light-emitting particle is determined at the resolution of the size of the observed subregion. Furthermore, from the distance between the appearance position of the peak of the signal of the light-emitting particle and a specific position (the center or an edge) of an observed subregion, the position (coordinates) of a light-emitting particle can be determined in detail (refer to FIG. 4C). Thus, when the position of a light-emitting particle is determined, by using this information, it will become possible to express the existence distribution of light-emitting particles in the region to be observed ObR as an image. Moreover, the existence distribution image of light-emitting particle may be represented while being superimposed on a microscopic image of the region to be observed ObR obtained by the other arbitrary microscopic observation method (phase-contrast microscopy, differential interference microscopy, epifluorescent microscopy, etc.) on the display of the computer 20. Concretely, there may be generated a plot image obtained by plotting the positions of light-emitting particles in a microscopic image obtained by an arbitrary microscopic observation method.

(iv) Determination of Light-Emitting Particle Concentration

When the number of light-emitting particles is determined by counting the number of signals of detected light-emitting particles, if the whole volume of the region through which the light detection region has passed is further computed by an arbitrary way, the concentration of the light-emitting particle can be determined from the volume value and the number of light-emitting particles. The whole volume of the region through which the light detection region has passed may be determined, for example, in the way described in patent document 1.

(v) Estimation of Size of Light-Emitting Particle

In the scanning molecule counting method, as described in patent document 6, when the signals of the same light-emitting particle have been detected multiple times, the displacement of the light-emitting particle in the scanning period is detected using the time points of the generations of those signals (at the times of the peaks), and the translational diffusional characteristic (for example, a diffusing constant) of the light-emitting particle can be estimated from the displacement. The translational diffusional characteristic is a function of the size of a light-emitting particle, and thereby, the estimation of the size of the detected light-emitting particle becomes possible. Thus, also in the inventive microscopic observation technique, using generation time points of signals of a light-emitting particle detected within each observed subregion, the estimation of a translational diffusional characteristic of the light-emitting particle and the size of the light-emitting particle may be performed. Its concrete processes may be performed in the way described in patent document 6. Moreover, as in the example of FIG. 8, in a case that the integration of light intensity is carried out before the detection of a signal of a light-emitting particle, it is possible to estimate a translational diffusional characteristic with reference to the width d of the integrated signal of the light-emitting particle (The larger the diffusing constant of a light-emitting particle is, the larger its displacement within scan time becomes, and the width d of the integrated signal increases).

In addition, in the scanning molecule counting method, the polarization characteristic or a rotational diffusion characteristic (for example, polarization degree) of a light-emitting particle can be measured by detecting polarized light components of detected light separately as described in patent document 7. Especially, because a rotational diffusion characteristic is a function of the size of a light-emitting particle, the size of a detected light-emitting particle can be estimated. Then, also in the inventive microscopic observation technique, the estimation of the polarization characteristic or the rotational diffusion characteristic of a light-emitting particle and the size of the light-emitting particle, detected within each observed subregion, by detecting the light from a light detection region while dividing it into two or more polarized light components and using the polarized light component intensities. Concrete processed may be performed in the way described in patent document 7.

As noted above, when the concentration, translational diffusional characteristic, polarization characteristic or rotational diffusion characteristic and/or size of a light-emitting particle are estimated, those values are represented in conjunction with an image expressing the existence distribution of the light-emitting particle. Alternatively, the respective characteristic values obtained in each observed subregion may be displayed as an image expressing the distribution of the concentration, translational diffusional characteristic, polarization characteristic or rotational diffusion characteristic and/or size of the light-emitting particle. Moreover, these characteristics of the light-emitting particle may be represented while being superimposed on a microscopic image of a cell or a cell organelle, etc., obtained by the other arbitrary microscopic observation method. Thereby, it becomes possible to grasp a characteristic of a light-emitting particle which exists in a cell or a cell organelle while its position in the cell or the cell organelle is specified.

Thus, according to the above-mentioned inventive microscopic observation technique, by conducting multiple times of scanning with a light detection region in each observed subregion in a region to be observed, and carrying out the individual detection of light-emitting particles by the scanning molecule counting method, the formation of an image expressing the existence distribution of light-emitting particles whose positions vary dynamically in a thick sample becomes possible. According to this feature, especially, it becomes possible to detect individually the existence position of a light-emitting particle in a cell or a cell organelle, and this is expected to be used advantageously in the research of cells and/or cell organelles, etc.

The invention claimed is:

1. An optical microscope device which detects light from a light-emitting particle in a sample liquid to detect the light-emitting particle, using an optical system of a confocal microscope or a multiphoton microscope, the device comprising:

a light detection region mover which moves a position of a light detection region multiple times continuously within each observed subregion, the respective observed subregions being obtained by dividing a region to be observed in a field of view of the microscope into plural regions;

a light detector which detects the light from the light detection region; and a signal processor which generates time series light intensity data of the light from the light detection region detected by the light detector while moving the position of the light detection region in each observed subregion, detects a signal having a profile of a light intensity variation indicating light from the light-emitting particle in the time series light intensity data, and determines a position of the light-emitting particle corresponding to the detected signal in the region to be observed, the position being at least an X coordinate and a Y coordinate of a subregion in the region to be observed, in which the light-emitting particle is detected, wherein the light detection region mover is a stage position changing apparatus or a galvano mirror device.

2. The device of claim 1, wherein the moving of the position of the light detection region in each observed subregion is conducted continuously in at least two directions for each observed subregion.

3. The device of claim 1, wherein the moving of the position of the light detection region in each observed subregion is conducted multiple times in one same direction for each observed subregion.

4. The device of claim 1, wherein the size of the observed subregion is determined based on the size of the light detection region.

5. The device of claim 1, wherein a size of the observed subregion is set such that a moving length of a light-emitting particle to be detected within a time in which the position of the light detection region is moved in the observed subregion becomes smaller than the size of the observed subregion.

6. The device of claim 1, wherein a length of one side edge of the Observed subregion is almost equal to a diameter of the light detection region; and one time of the moving of the position of the light detection region in each observed subregions is carried out from when a front edge in a moving direction of the light detection region passes through one side edge of the observed subregion and until a rear edge in the moving direction of the light detection region arrives at another side edge of the observed subregion.

7. The device of Claim 1, wherein the device produces a plot image obtained by plotting a position of the light-emitting particle whose position in the region to be observed has been determined in a microscopic image of the region to be observed generated by an arbitrary way.

8. The device of claim 1, wherein the signal processor determines information about a size of the light-emitting particle by using a characteristic of signals of one same light-emitting particle obtained through the multiple times of moving of the light detection region in each observed subregion.

9. The device of claim 8, wherein the characteristic of the signals of the light-emitting particle used for determining the information about the size of the light-emitting particle is an index value expressing a translational diffusional characteristic of the light-emitting particle or an index value expressing a rotational diffusion characteristic of the light-emitting particle.

10. The device of claim 1, wherein the signal processor determines the number of the light-emitting particle in the region to be observed or a concentration of the light-emitting particle in the liquid based on the number of the detected light-emitting particle.

11. An optical microscopic observation method of detecting light from a light-emitting particle in a sample liquid to detect the light-emitting particle, using an optical system of a confocal microscope or a multiphoton microscope, comprising the steps of:

(a) moving a position of a light detection region continuously multiple times within each observed subregion obtained by dividing a region to be observed within a field of view of the microscope into plural regions;

(b) detecting light from the light detection region by a light detector; and (c) generating time series light intensity data of the light from the light detection region detected by the light detector while moving the position of the light detection region in each observed subregion, detecting a signal having a profile of a light intensity variation indicating light from the light-emitting particle in the time series light intensity data, and determining a position of the light-emitting particle corresponding to the detected signal in the region to be observed, the position being at least an X coordinate and a Y coordinate of a subregion, in the region to be observed, in which the light-emitting particle is detected.

12. A computer readable storage device having a computer program product including programmed instructions for observation with an optical microscope for detecting light from a light-emitting particle in a sample liquid to detect the light-emitting particle, using an optical system of a confocal microscope or a multiphoton microscope, said programmed instructions causing a computer to perform the steps of:

moving a position of a light detection region continuously multiple times within each observed subregion obtained by dividing a region to be observed within a field of view of the microscope into plural regions;

detecting light from the light detection region by a light detector; and generating time series light intensity data of the light from the light detection region detected by the light detector while moving the position of the light detection region in each observed subregion, detecting a signal having a profile of a light intensity variation indicating light from the light-emitting particle in the time series light intensity data, and determining a position of the light-emitting particle corresponding to the detected signal in the region to be observed, the position being at least an X coordinate and a Y coordinate of a subregion, in the region to be observed, in which the light-emitting particle is detected.

* * * * *